(12) United States Patent
Kakinuma

(10) Patent No.: US 11,407,846 B2
(45) Date of Patent: Aug. 9, 2022

(54) (METH)ACRYLATE, MONOMER COMPOSITION, DENTAL MATERIAL OBTAINED FROM COMPOSITION, AND PRODUCTION METHOD THEREOF

(71) Applicant: MITSUI CHEMICALS, INC., Tokyo (JP)

(72) Inventor: Naoyuki Kakinuma, Ichihara (JP)

(73) Assignee: MITSUI CHEMICALS, INC., Tokyo (JP)

( * ) Notice: Subject to any disclaimer, the term of this patent is extended or adjusted under 35 U.S.C. 154(b) by 0 days.

(21) Appl. No.: 16/760,279

(22) PCT Filed: Nov. 27, 2018

(86) PCT No.: PCT/JP2018/043466
§ 371 (c)(1),
(2) Date: Apr. 29, 2020

(87) PCT Pub. No.: WO2019/107322
PCT Pub. Date: Jun. 6, 2019

(65) Prior Publication Data
US 2020/0325255 A1    Oct. 15, 2020

(30) Foreign Application Priority Data

Nov. 28, 2017 (JP) .............................. JP2017-227836
Nov. 28, 2017 (JP) .............................. JP2017-227838

(51) Int. Cl.
| C08F 20/06 | (2006.01) |
| A61K 6/887 | (2020.01) |
| A61K 6/71 | (2020.01) |
| A61K 6/54 | (2020.01) |

(52) U.S. Cl.
CPC .............. *C08F 20/06* (2013.01); *A61K 6/54* (2020.01); *A61K 6/71* (2020.01); *A61K 6/887* (2020.01)

(58) Field of Classification Search
CPC ................................................ A61K 6/887
See application file for complete search history.

(56) References Cited

U.S. PATENT DOCUMENTS

| 4,609,718 | A | * | 9/1986 | Bishop ................. C03C 25/106 |
| | | | | 385/128 |
| 4,798,852 | A | | 1/1989 | Zimmerman et al. |
| 4,879,402 | A | | 11/1989 | Reiners et al. |
| 4,952,241 | A | | 8/1990 | Reiners et al. |
| 5,674,942 | A | | 10/1997 | Hill et al. |
| 6,653,375 | B2 | | 11/2003 | Moszner et al. |
| 6,794,422 | B1 | | 9/2004 | Bruchmann et al. |
| 7,064,174 | B2 | | 6/2006 | Lewis et al. |
| 9,011,150 | B2 | | 4/2015 | Sun |
| 9,212,251 | B2 | | 12/2015 | Frick et al. |
| 9,511,004 | B2 | | 12/2016 | Naruse et al. |
| 9,937,105 | B2 | | 4/2018 | Sun |
| 10,130,563 | B2 | | 11/2018 | Yoshinaga et al. |
| 10,130,564 | B2 | | 11/2018 | Yoshinaga et al. |
| 2002/0082315 | A1 | | 6/2002 | Moszner et al. |
| 2003/0152786 | A1 | | 8/2003 | Lewis et al. |
| 2008/0015310 | A1 | | 1/2008 | Tong |
| 2012/0129973 | A1 | | 5/2012 | Sun |
| 2012/0296003 | A1 | | 11/2012 | Naruse et al. |
| 2015/0196462 | A1 | | 7/2015 | Sun |
| 2017/0174621 | A1 | | 6/2017 | Yoshinaga et al. |
| 2017/0181932 | A1 | | 6/2017 | Yoshinaga et al. |

FOREIGN PATENT DOCUMENTS

| DE | 40 25 776 A1 | 2/1992 |
| JP | S61-276862 A | 12/1986 |
| JP | S63-035550 A | 2/1988 |
| JP | H11-315059 A | 11/1999 |
| JP | 2000-204069 A | 7/2000 |
| JP | 2000-313735 A | 11/2000 |
| JP | 2003-511497 A | 3/2003 |
| JP | 2003-522227 A | 7/2003 |
| JP | 2013-544823 A | 12/2013 |
| WO | 2012/157566 A1 | 11/2012 |
| WO | 2015/152221 A1 | 10/2015 |

OTHER PUBLICATIONS

Ellrich et al. (DE 40 25 776) English machine translation (Year: 1992).*
Jeffamine Polyetheramine, Hunstman Corporation, 2021.*
International Search Report (Form PCT/ISA/210) and Written Opinion of the International Searching Authority (Form PCT/ISA/237) dated Mar. 5, 2019, by the Japan Patent Office in corresponding International Application No. PCT/JP2018/043466. (8 pages).

* cited by examiner

*Primary Examiner* — Michael F Pepitone
(74) *Attorney, Agent, or Firm* — Buchanan Ingersoll & Rooney PC

(57) ABSTRACT

Provided are a monomer which can provide a cured product having both high toughness and rigidity, a monomer composition containing the monomer, the monomer composition used as a dental material monomer composition, a dental material composition containing the monomer composition or the dental material monomer composition, a cured product thereof having excellent mechanical properties, a dental material formed by curing the dental material composition, a method for producing the monomer composition, and a method for producing the dental material. A (meth)acrylate (D) is a reaction product of an amine compound (A) having two or more amino groups, an iso(thio)cyanate compound (B) having two or more iso(thio)cyanato groups, and a hydroxy (meth)acrylate compound (C) having one or more polymerizable groups.

22 Claims, 3 Drawing Sheets

[Figure 1]
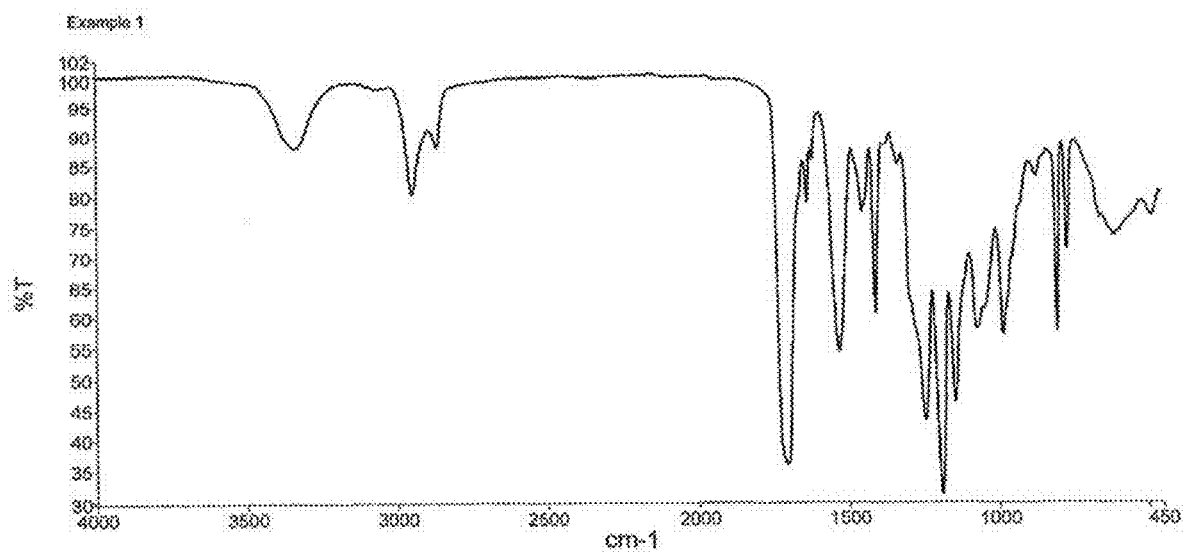
[Figure 2]
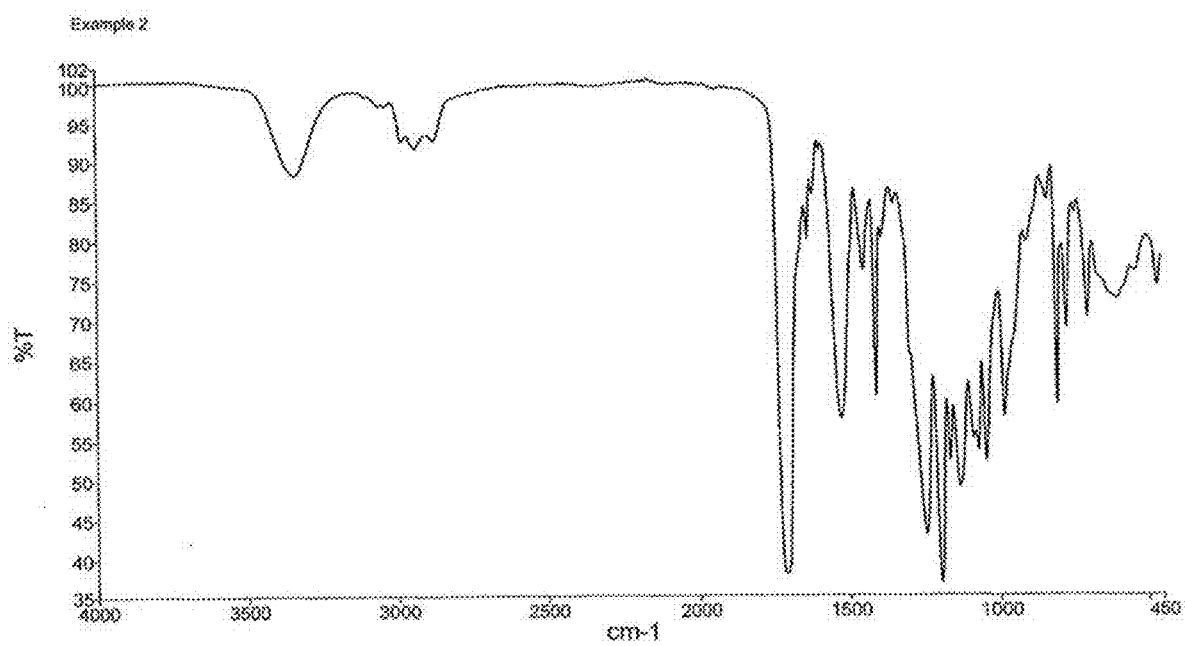

[Figure 3]
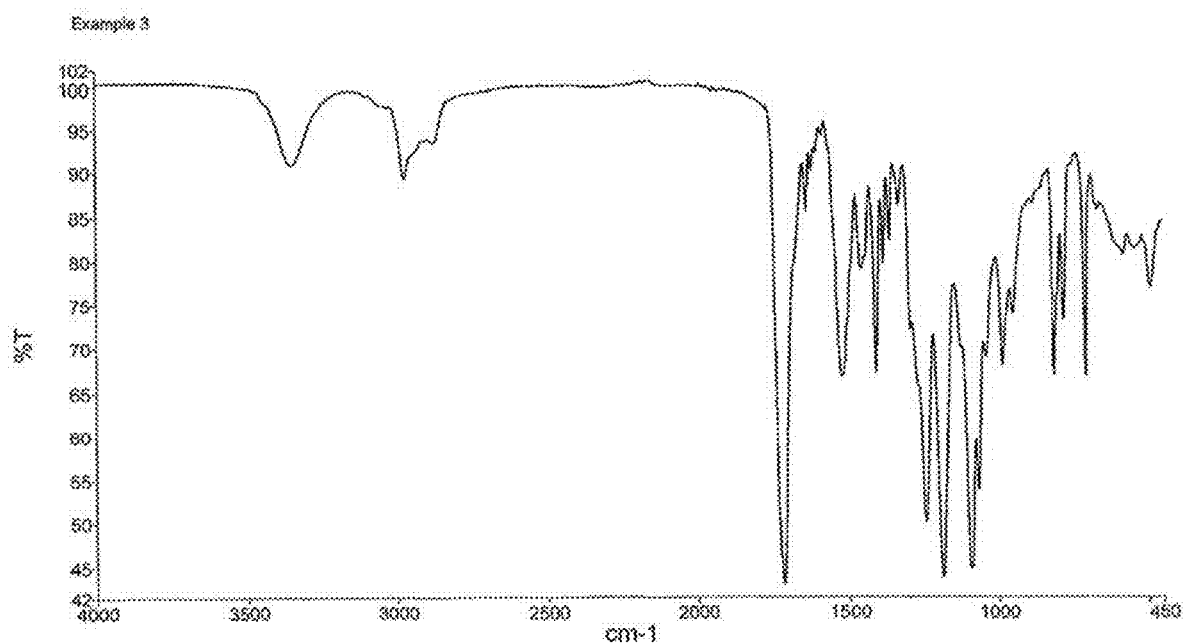
[Figure 4]
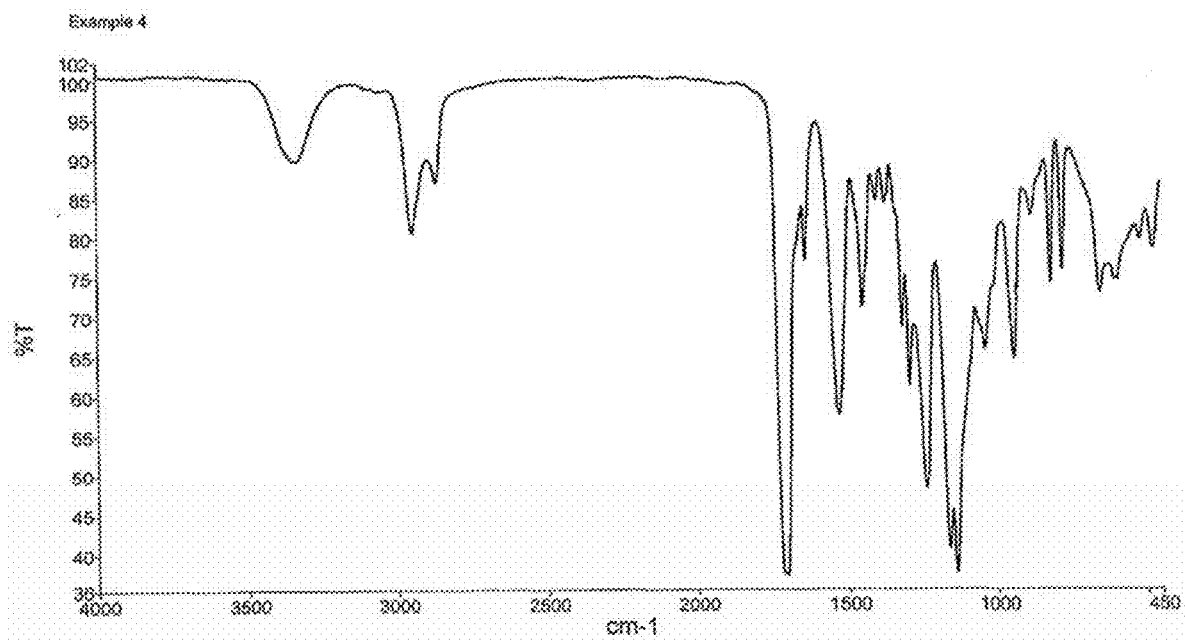

[Figure 5]
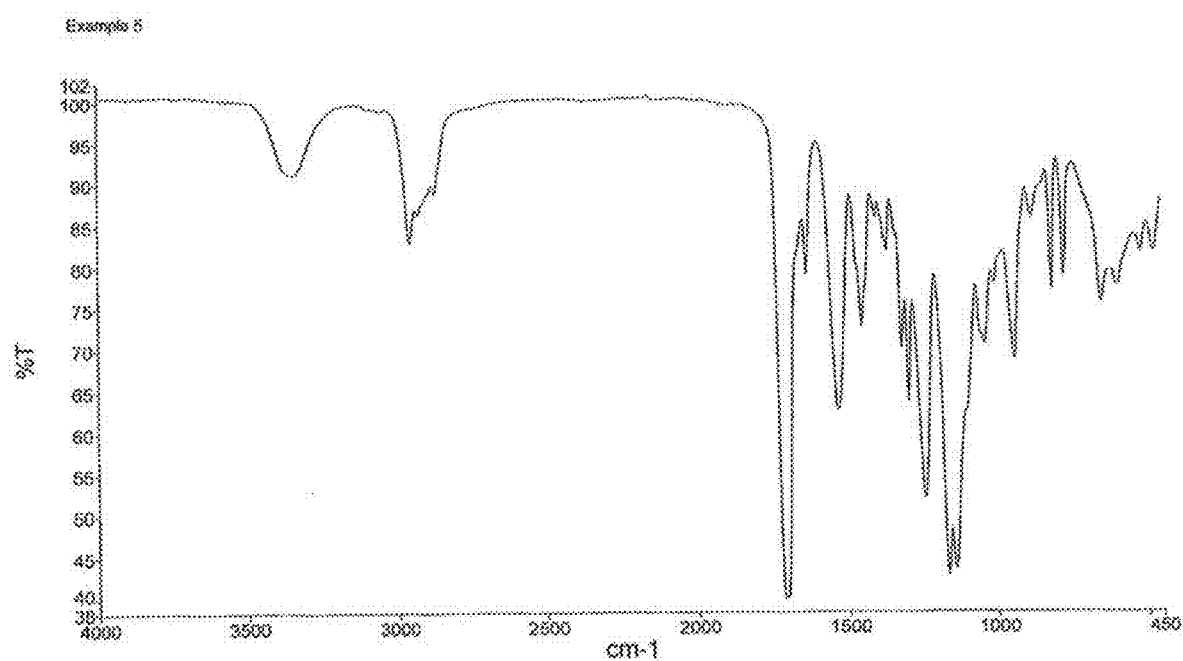

(METH)ACRYLATE, MONOMER COMPOSITION, DENTAL MATERIAL OBTAINED FROM COMPOSITION, AND PRODUCTION METHOD THEREOF

CROSS-REFERENCE TO RELATED APPLICATIONS

This application is a U.S. national stage application of PCT/JP2018/043466, filed on Nov. 27, 2018, which in turn claims priority to Japanese Patent Application No. 2017-227836, filed on Nov. 28, 2017, and Japanese Patent Application No. 2017-227836, filed on Nov. 28, 2017, the entire contents of all of which are hereby incorporated by reference.

TECHNICAL FIELD

The present invention relates to a novel (meth)acrylate, a monomer composition containing the (meth)acrylate, the monomer composition used as a dental material monomer composition, a dental material composition containing the monomer composition, and a cured product obtained by curing the dental material composition.

BACKGROUND ART

Composite resins which are a typical example of dental material compositions typically contain a monomer composition containing a monomer, a filler, a polymerization initiator, a polymerization inhibitor, a dye, and the like. Looking at the weight ratio of each component in such a composite resin, the filler usually has the largest weight ratio, followed by a monomer composition, and these two components account for most of the weight of the composite resin. The monomer composition serves as a binder for the filler. The properties of monomers, and the properties of cured products thereof are significantly influential on the properties and performance of the composite resin containing the monomer composition, and cured products thereof.

From the viewpoints of such as the biological safety of monomers and the mechanical strength and wear resistance of cured products, radically polymerizable polyfunctional methacrylate compositions are frequently used as the monomer compositions. As a typical example, the polyfunctional methacrylate compositions mainly contain 2,2-bis[4-(3-methacryloyloxy-2-hydroxypropoxy)phenyl]propane (hereinafter, referred to as Bis-GMA) or 2,2,4-trimethylhexamethylenebis(2-carbamoyloxyethyl)dimethacrylate (hereinafter, referred to as UDMA), and contain triethylene glycol dimethacrylate (hereinafter, referred to as TEGDMA) to adjust the viscosity.

In the dental clinical practice, the restoration of tooth defects using composite resins has a long history, and the use range of the composite resins is also expanding. However, the mechanical properties of a composite resin cured product are still insufficient. In particular, under an actual condition, the poor strength obstructs the application of the resins to sites subjected to a high stress, for example, molar tooth crowning materials.

In recent years, the clinical practice strongly demands the expansion of the application of composite resins to such high-stress sites. Therefore, the development of composite resins having higher mechanical properties is an urgent necessity. As described above, the properties of cured products of monomer compositions contained in composite resins significantly affect the properties of cured products of the composite resins containing the compositions.

There have been reported, as examples, trials to use monomers replacing Bis-GMA and UDMA which are widely used as main components of monomer compositions so as to enhance the mechanical strength of cured products of composite resins (Patent Literature 1 and Patent Literature 2).

Examples of trials to improve main component monomers include an enhancement in main component monomers so as to enhance the refractive index of cured products of monomer compositions (Patent Literature 3), and an enhancement in main component monomers so as to enhance the polymerization shrinkage before and after the curing of monomer compositions (Patent Literature 4).

CITATION LIST

Patent Literature

Patent Literature 1: Japanese Patent Laid-Open No. 2000-204069
Patent Literature 2; National Publication of International Patent Application No. 2013-544823
Patent Literature 3: Japanese Patent Laid-Open No. 11-315059
Patent Literature 4: International Publication No. WO2012-157566

SUMMARY OF INVENTION

Technical Problem

As described above, the expansion of the application ranges of dental material compositions containing monomers or monomer compositions including composite resins makes it necessary to enhance the mechanical properties of cured products of the dental material compositions.

In view of the problems, it is an object of the present invention to provide a monomer which can provide a cured product having both high toughness and rigidity, a monomer composition containing the monomer, the monomer composition used as a dental material monomer composition, a dental material composition containing the monomer composition or the dental material monomer composition, a cured product thereof having excellent mechanical properties, a dental material formed by curing the dental material composition, a method for producing the monomer composition, and a method for producing the dental material.

Solution to Problem

After extensive studies, the present inventors have found that a cured product of a monomer composition containing a urethane urea type (meth)acrylate obtained from an appropriately rigid polyfunctional iso(thio)cyanate, a specific amine compound, and an appropriately flexible hydroxy (meth)acrylate exhibits high mechanical properties, and have completed the present invention.

The present invention provides a (meth)acrylate, a monomer composition containing the (meth)acrylate, a molded body obtained by curing the monomer composition, a dental material composition containing the monomer composition, and a cured product of the dental material composition, including the following [1] to [20].

[1]

A (meth)acrylate (D) which is a reaction product of an amine compound (A) having two or more amino groups, an iso(thio)cyanate compound (B) having two or more iso(thio)cyanato groups, and a hydroxy (meth)acrylate compound (C) having one or more polymerizable groups.

[2]

The (meth)acrylate (D) according to [1], wherein the (meth)acrylate (D) has a structure represented by the following general formula (D1) and a structure represented by the following general formula (D2):

[Chem. 1]

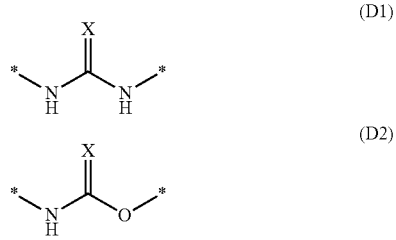

wherein
X represents an oxygen atom or a sulfur atom; and
* represents a point of attachment.

[3]

The (meth)acrylate (D) according to [1], wherein the (meth)acrylate (D) is represented by the following general formula (1):

[Chem. 2]

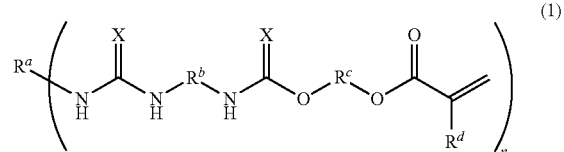

wherein
$R^a$ is a residue excluding all amino groups from an amine compound (A1) having two or three amino groups;
$R^b$ is a residue excluding all iso(thio)cyanato groups from an iso(thio)cyanate compound (B1) having two iso(thio)cyanato groups;
$R^c$ is a residue excluding one (meth)acryloyloxy group and one hydroxy group from the hydroxy (meth)acrylate compound (C);
$R^d$ represents a hydrogen atom or a methyl group;
X represents an oxygen atom or a sulfur atom;

n represents the number of all the amino groups contained in the amine compound (A); and
a plurality of $R^b$, $R^c$, $R^d$, and X may each be the same as or different from each other.

[4]

The (meth)acrylate (D) according to [1], wherein the (meth)acrylate (D) is represented by the following general formula (2):

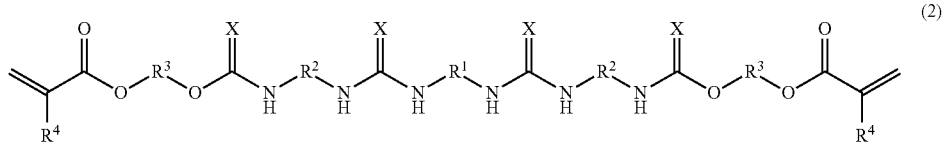

wherein
$R^1$ is a group in which a central part is bonded to two end parts;
the end part is bonded to a NH group adjacent to the end part;
the central part is a divalent hydrocarbon group;
an ethylene group contained in the divalent hydrocarbon group may be substituted with an oxyethylene group, or a propylene group contained in the divalent hydrocarbon group may be substituted with an oxypropylene group;
the end part is a methylene group which may have a substituent group;
each $R^2$ is independently a group in which a central part is bonded to two end parts;
the end part is bonded to a NH group adjacent to the end part;
the central part is a $C_{5-12}$ divalent aromatic hydrocarbon group, a $C_{5-12}$ divalent acyclic hydrocarbon group, or a $C_{5-12}$ divalent alicyclic hydrocarbon group;
the end part is a methylene group which may have a substituent group;
each $R^3$ is independently a $C_{2-6}$ linear alkylene group or a $C_{2-6}$ linear oxyalkylene group in which a hydrogen atom may be substituted with a $C_{1-3}$ alkyl group or a (meth)acryloyloxymethylene group;
$R^4$ each independently represents a hydrogen atom or a methyl group;
X is O or S; and
a plurality of $R^2$, $R^3$, $R^4$, and X may each be the same as or different from each other.

[5]

The (meth)acrylate (D) according to [4], wherein in the general formula (2), $R^1$ is a group represented by the following formula (3):

[Chem. 4]

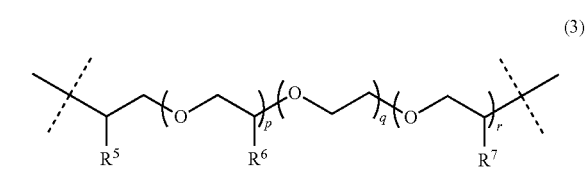

wherein
$R^5$ to $R^7$ each represent a hydrogen atom or a methyl group;

p represents an integer of 0 to 100;
q represents an integer of 0 to 100;
r represents an integer of 1 to 100;
p+r satisfies an integer of 1 to 101; and
when a plurality of $R^6$ or $R^7$ are present, the plurality of $R^6$ or the plurality of $R^7$ may be the same as or different from each other.

[6]

The (meth)acrylate (D) according to [4] or [5], wherein $R^1$ has an average molecular weight of 300 to 2000.

[7]

The (meth)acrylate (D) according to any one of [4] to [6], wherein each $R^2$ is independently a group represented by the following formula (4), (5), (6), or (7).

[Chem. 5]

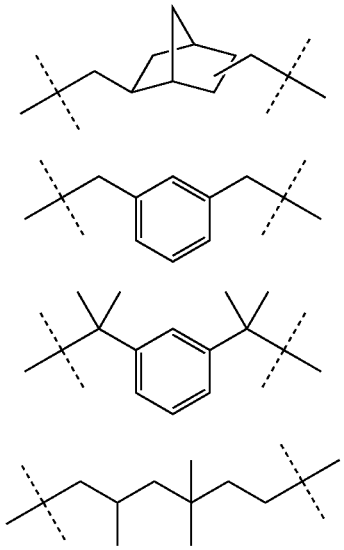

(4)

(5)

(6)

(7)

[8]

The (meth)acrylate (D) according to any one of [3] to [7], wherein each $R^3$ is independently a $C_{2-6}$ linear alkylene group or a $C_{2-6}$ linear oxyalkylene group in which a hydrogen atom may be substituted with a $C_{1-3}$ alkyl group.

[9]

The (meth)acrylate (D) according to [1] or [2], wherein the amine compound (A) is at least one amine compound selected from a compound (a1) represented by the general formula (a1-1) and a compound (a2) represented by the general formula (a2-1):

[Chem. 6]

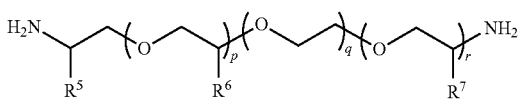

(a1-1)

wherein
$R^5$ to $R^7$ each represent a hydrogen atom or a methyl group;
p represents an integer of 0 to 100;
q represents an integer of 0 to 100;
r represents an integer of 1 to 100;
p+r satisfies an integer of 1 to 101; and
when a plurality of $R^6$ or $R^7$ are present, the plurality of $R^6$ or the plurality of $R^7$ may be the same as or different from each other; and

[Chem. 7]

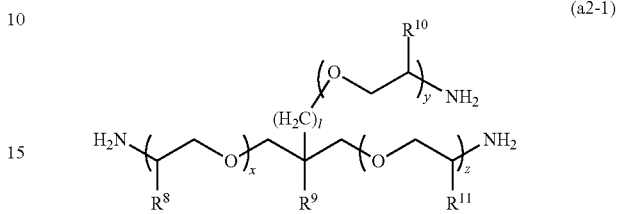

(a2-1)

wherein
$R^8$, $R^{10}$, and $R^{11}$ each represent a hydrogen atom or a methyl group:
$R^9$ represents a $C_{1-20}$ linear acyclic alkyl group, a $C_{3-20}$ branched acyclic alkyl group, or a $C_{3-20}$ alicyclic alkyl group;
x+y+z represents an integer of 1 to 200;
l represents an integer of 0 to 10; and
when a plurality of $R^8$, $R^{10}$, or $R^{11}$ are present, the plurality of $R^8$, the plurality of $R^{10}$, or the plurality of $R^{11}$ may be the same as or different from each other.

[10]

The (meth)acrylate (D) according to [1], [2], or [9], wherein a ratio (a/b) of a number of moles of the amino groups of the amine compound (A), a, to a number of moles of the iso(thio)cyanato groups of the iso(thio)cyanate compound (B), b, is 0.01 to 0.20.

[11]

The (meth)acrylate (D) according to [9] or [10], wherein the iso(thio)cyanate compound (B) is at least one selected from the group consisting of hexamethylene diisocyanate, 2,2,4-trimethylhexane diisocyanate, 2,4,4-trimethylhexamethylene diisocyanate, pentamethylene diisocyanate, m-xylylene diisocyanate, isophorone diisocyanate, bis(isocyanatomethyl)cyclohexane, bis(isocyanatocyclohexyl)methane, 2,5-bis(isocyanatomethyl)bicyclo-[2.2.1]-heptane, 2,6-bis(isocyanatomethyl)bicyclo-[2.2.1]-heptane, tolylene diisocyanate, phenylene diisocyanate, and 4,4'-diphenylmethane diisocyanate.

[12]

The (meth)acrylate (D) according to any one of [1] to [11], wherein the (meth)acrylate (D) has a viscosity of 1 to 100,000 mPa·s at 25° C.

[13]

A monomer composition comprising the (meth)acrylate (D) according to any one of [1] to [12].

[14]

The monomer composition according to [13], wherein the monomer composition is a dental material monomer composition.

[15]

The monomer composition according to [13] or [14], wherein the monomer composition contains a polymerizable compound (E) containing at least one polymerizable group selected from a methacryloyl group and an acryloyl group (excluding a (meth)acrylate (D)).

[16]
A molded body obtained by curing the monomer composition according to any one of [13] to [15].
[17]
A dental material composition comprising:
the monomer composition according to any one of [13] to [15];
a polymerization initiator; and
a filler.
[18]
A dental material obtained by curing the dental material composition according to [17].
[19]
A method for producing a monomer composition, comprising the steps of:
(i) reacting an amine compound (A) having two or more amino groups with an isocyanate compound (B) having two or more iso(thio)cyanato groups to obtain an intermediate; and
(ii) reacting the intermediate with a hydroxy (meth)acrylate compound (C) having one or more polymerizable groups.
[20]
A method for producing a dental material, comprising the steps of:
injecting the dental material composition according to [17] into a casting mold; and
curing the dental material composition in the casting mold.

Advantageous Effects of Invention

The cured product having both high toughness and rigidity is obtained from the monomer composition containing the (meth)acrylate of the present invention. The cured product has high mechanical properties.

BRIEF DESCRIPTION OF DRAWINGS

FIG. 1 shows an IR spectrum of a composition containing a (meth)acrylate (D-3) obtained in Example 3.
FIG. 2 shows an IR spectrum of a composition containing a (meth)acrylate (D-6) obtained in Example 6.
FIG. 3 shows an IR spectrum of a composition containing a (meth)acrylate (D-9) obtained in Example 9.
FIG. 4 shows an IR spectrum of a composition containing a (meth)acrylate (D-12) obtained in Example 12.
FIG. 5 shows an IR spectrum of a composition containing a (meth)acrylate (D-15) obtained in Example 15.

DESCRIPTION OF EMBODIMENTS

Hereinafter, a (meth)acrylate and the like of the present invention will be described in detail.
[(Meth)acrylate (D)]
A (meth)acrylate (D) of the present invention is a reaction product of an amine compound (A) having two or more amino groups, an iso(thio)cyanate compound (B) having two or more iso(thio)cyanato groups, and a hydroxy (meth)acrylate compound (C) having one or more polymerizable groups. The (meth)acrylate (D) is usually a monomer which can be polymerized, and can be used as one component of a polymerizable composition, for example. Herein, the iso(thio)cyanato group means an isocyanato group (—NCO) or an isothiocyanato group (—NCS), and the iso(thio)cyanate means isocyanate or isothiocyanate. Herein, the (meth)acrylate means acrylate or methacrylate.

When a compound having an isocyanato group is used as the iso(thio)cyanate compound (B), the (meth)acrylate (D) is a urethane urea (meth)acrylate. When a compound having an isothiocyanato group is used, the (meth)acrylate (D) is a (meth)acrylate having a structure in which C=O constituting urethane urea in the urethane urea (meth)acrylate is substituted with C=S. In the present invention, both the (meth)acrylates are sometimes collectively referred to as a urethane urea type (meth)acrylate. The urethane urea type (meth)acrylate (D) is preferably a urethane urea (meth) acrylate from the viewpoint of mechanical properties.

The (meth)acrylate (D) may or may not have an amino group. For example, in the reaction of the amino groups of the amine compound (A), the iso(thio)cyanate compound (B), and the hydroxy (meth)acrylate (C), all the amino groups of the amine compound (A) may be reacted, or some amino groups may not be reacted. In this case, a mixture of the (meth)acrylate (D) which is a reaction product and the unreacted amine compound (A) may be generated. The presence or absence of the amino groups can be confirmed by FT-IR measurement, for example.

The (meth)acrylate (D) may or may not have an iso(thio) cyanato group. For example, in the reaction of the amine compound (A), the iso(thio)cyanate compound (B), and the hydroxy (meth)acrylate (C), all the iso(thio)cyanato groups of the iso(thio)cyanate compound (B) may be reacted, or some iso(thio)cyanato groups of the iso(thio)cyanate compound (B) may not be reacted. In this case, a mixture of the (meth)acrylate (D) which is a reaction product and the unreacted iso(thio)cyanate compound (B) may be generated. The presence or absence of the iso(thio)cyanato group can be confirmed by FT-IR measurement, for example.

The (meth)acrylate (D) may have an amino group and/or an iso(thio)cyanato group, and may further have a hydroxy group. For example, in the reaction of the amine compound (A), the iso(thio)cyanate compound (B), and the hydroxy (meth)acrylate (C), some hydroxy groups of the hydroxy (meth)acrylate compound (C) may not be reacted. In this case, a mixture of the (meth)acrylate (D) which is a reaction product and the unreacted hydroxy (meth)acrylate compound (C) may be generated. The presence or absence of the (meth)acryloyloxy group can be confirmed by FT-IR measurement, for example.

The (meth)acrylate (D) preferably has a structure represented by the following general formula (D1) and formed by a reaction between the amino group contained in the amine compound (A) and the iso(thio)cyanato group contained in the iso(thio)cyanate compound (B) and has a structure represented by the following general formula (D2) and formed by a reaction between the iso(thio)cyanato group contained in the iso(thio)cyanate compound (B) and the hydroxy group contained in the hydroxy (meth)acrylate compound (C).

[Chem. 8]

(D1)

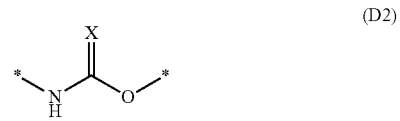

(D2)

In the general formulas (D1) and (D2), X represents an oxygen atom or a sulfur atom, and * represents a point of attachment. X is preferably an oxygen atom from the viewpoint of mechanical properties.

The amine compound (A) is preferably an amine compound (A1) having two or three amino groups from the viewpoint of the handleability of the obtained (meth)acrylate (D).

The iso(thio)cyanate compound (B) is preferably an iso(thio)cyanate compound (B1) having two iso(thio)cyanato groups from the viewpoint of the handleability of the obtained (meth)acrylate (D).

In the (meth)acrylate (D), a (meth)acrylate represented by the following general formula (1) is preferred. The (meth)acrylate is obtained by first producing a precursor having an iso(thio)cyanato group at its terminal, and obtained by reacting the amine compound (A1) and the iso(thio)cyanate compound (B1) with each other, and reacting the terminal iso(thio)cyanato group of the precursor and one hydroxy group contained in the hydroxy (meth)acrylate compound (C) with each other.

[Chem. 9]

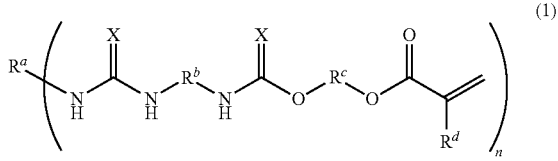

In the general formula (1), $R^a$ is a residue excluding all amino groups from an amine compound (A1) having two or three amino groups; $R^b$ is a residue excluding all iso(thio)cyanato groups from an iso(thio)cyanate compound (B1) having two iso(thio)cyanato groups; $R^c$ is a residue excluding one (meth)acryloyloxy group and one hydroxy group from the hydroxy (meth)acrylate compound (C); $R^d$ represents a hydrogen atom or a methyl group; X represents an oxygen atom or a sulfur atom; and n represents the number of all the amino groups contained in the amine compound (A). A plurality of $R^b$, $R^c$, $R^d$, and X may each be the same as or different from each other.

In the general formula (1), $R^a$ is a group in which a central part is bonded to two or three end parts; the end part is bonded to a NH group adjacent to the end part; the central part is a $C_{2-700}$ divalent or trivalent hydrocarbon group; an alkylene group contained in the divalent or trivalent hydrocarbon group may contain an oxygen atom; and the end part is preferably a methylene group which may have a substituent group.

From the viewpoint of the handleability of the obtained (meth)acrylate (D), the amine compound (A1) is preferably at least one amine compound selected from a compound (a1) represented by the following general formula (a1-1) later and a compound (a2) represented by the following general formula (a2-1) which are described later.

In the (meth)acrylate (D), a (meth)acrylate (D1) obtained by using a compound (A2) having two amino groups as the amine compound (A) is a preferred aspect.

In the (meth)acrylate (D1), a compound represented by the following general formula (2) is preferred. Hereinafter, the compound represented by the following general formula (2) is also referred to as a (meth)acrylate (D1-1).

[Chem. 10]

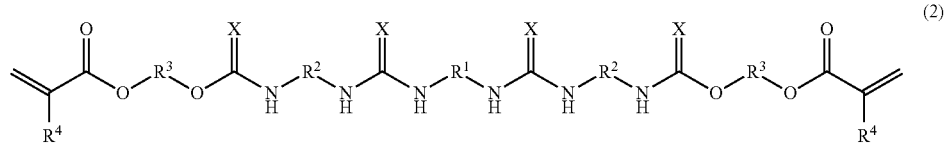

In the general formula (2), $R^1$ is a group in which a central part is bonded to two end parts; the end part is bonded to a NH group adjacent to the end part; the central part is a divalent hydrocarbon group; an ethylene group contained in the divalent hydrocarbon group as the central part may be substituted with an oxyethylene group, or a propylene group contained in the divalent hydrocarbon group as the central part may be substituted with an oxypropylene group; and the end part is a methylene group which may have a substituent group.

In the present invention, in the general formula (2), the divalent hydrocarbon group included in the central part in $R^1$ contains any one of ethylene groups of which at least one may be substituted with an oxyethylene group or propylene groups of which at least one may be substituted with an oxypropylene group.

Examples of the divalent hydrocarbon group of the central part include a divalent aliphatic hydrocarbon group, a divalent alicyclic ring-containing hydrocarbon group, or a divalent aromatic ring-containing hydrocarbon group. The divalent hydrocarbon group of the central part is preferably a $C_{6-120}$ divalent hydrocarbon group.

Examples of the divalent aliphatic hydrocarbon group include a divalent linear or branched aliphatic hydrocarbon group.

Examples of the linear aliphatic hydrocarbon group include linear alkylene groups such as hexylene groups (hexamethylene groups), hepthylene groups (heptamethylene groups), octhylene groups (octamethylene groups), nonylene groups, decylene groups, isodecylene groups, dodecylene groups, tetradecylene groups, hexadecylene groups and octadecylene groups, linear alkynylene groups such as octenylene groups, decenylene groups, undecenylene groups, dodecenylene groups, tetradecenylene groups, hexadecenylene groups and octadecenylene groups, and linear alkenylene groups such as octenylene groups.

Examples of the branched aliphatic hydrocarbon group include branched alkylene groups such as diethylpropylene groups and 2-ethylhexylene groups, $C_{3-18}$ branched alkenylene groups such as methyl ethynylene groups, methyl propenylene groups, and methyl butenylene groups, and $C_{4-8}$ branched alkynylene groups such as methyl propynylene groups and methyl butynylene groups.

Examples of the alicyclic ring-containing hydrocarbon group include a divalent alicyclic ring-containing hydrocarbon group. The alicyclic ring-containing hydrocarbon group may contain one or more alicyclic hydrocarbons in its hydrocarbon group. For example, the aliphatic hydrocarbon group and the like may be bonded to the alicyclic hydrocarbon, for example.

More specific examples of the alicyclic ring-containing hydrocarbon group include cycloalkylene groups such as cyclohexylene groups, cycloheptylene groups, and cyclooctylene groups. Examples of the alicyclic ring-containing hydrocarbon group containing an aliphatic hydrocarbon group include methyl cyclohexylene groups, hydrogenated xylylene groups, hydrogenated tetramethylxylylene groups, cyclohexyl methylene groups, isophorone groups, norbornylane groups, and adamantylene groups.

Examples of the aromatic ring-containing hydrocarbon group include a divalent aromatic ring-containing hydrocarbon group. The aromatic ring-containing hydrocarbon group may contain one or more aromatic hydrocarbons in its hydrocarbon group. For example, the aliphatic hydrocarbon group and the like may be bonded to the aromatic hydrocarbon, for example.

More specific examples of the aromatic ring-containing hydrocarbon group include $C_{6-20}$ arylene groups such as phenylene groups, tolylene groups, dimethyl phenylene groups, naphthylene groups, biphenylene groups, and triphenylene groups, and aralkylene groups such as xylylene groups (phenylene bis(methylene)groups) and phenyl propylene groups.

At least one ethylene group contained in the $C_{6-120}$ divalent hydrocarbon group of the central part may be substituted with an oxyethylene group, or a propylene group contained in the hydrocarbon group may be substituted with an oxypropylene group.

The end part of $R^1$ is a methylene group which may have a substituent group, and examples of the substituent group include alkyl groups such as methyl groups.

The average molecular weight of the $R^1$ is preferably 300 to 2000.

One preferred aspect of $R^1$ of the general formula (2) is a group in which $R^1$ is represented by the following formula (3).

[Chem. 11]

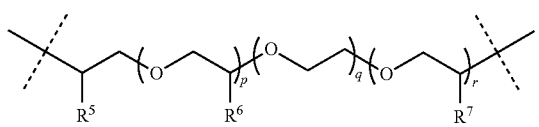

(3)

In the general formula (3), $R^5$ to $R^7$ each represent a hydrogen atom or a methyl group. p represents an integer of 0 to 100, preferably an integer of 0 to 70, and more preferably an integer of 0 to 35. q represents an integer of 0 to 100, preferably an integer of 0 to 70, and more preferably an integer of 0 to 40. r represents an integer of 1 to 101, preferably an integer of 1 to 70, and more preferably an integer of 1 to 35. p+r satisfies an integer of 1 to 101, preferably an integer of 1 to 71, and more preferably an integer of 1 to 36. When a plurality of $R^6$ or $R^7$ are present, the plurality of $R^6$ or the plurality of $R^7$ may be the same as or different from each other.

From the viewpoint of the advantageous effects of the present invention, it is preferred to use a compound represented by the general formula (3a), wherein both p and q as $R^1$ are 0.

[Chem. 12]

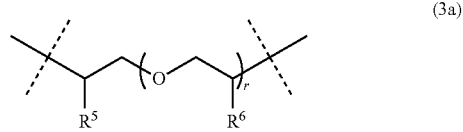

(3a)

In the general formula (3a), $R^5$, $R^7$, and r are as defined for $R^5$, $R^7$, and r of the general formula (3), respectively.

In the general formula (2), each $R^2$ is independently a group in which a central part is bonded to two end parts; the end part is bonded to a NH group adjacent to the end part; the central part is a $C_{5-12}$ divalent aromatic hydrocarbon group, a $C_{5-12}$ divalent acyclic hydrocarbon group, or a $C_{5-12}$ divalent alicyclic hydrocarbon group; and the end part is a methylene group which may have a substituent group.

From the viewpoint of having appropriate rigidity, the number of carbon atoms of the divalent aromatic hydrocarbon group, the divalent acyclic hydrocarbon group, or the divalent alicyclic hydrocarbon group as the central part of $R^2$ is usually 5 to 12, and preferably 6 to 12.

Examples of the $C_{5-12}$ alicyclic hydrocarbon group include an isophorone group, a cyclohexyl methylene group, and a bicyclo[2.2.1]heptylene group. Of these, from the viewpoint of the toughness of the cured product, a bicyclo[2.2.1]heptylene group is preferred.

Examples of the $C_{5-12}$ acyclic hydrocarbon group include a pentamethylene group, a hexamethylene group, and a trimethylhexamethylene group. Of these, from the viewpoint of the toughness of the cured product, a trimethylhexamethylene group is preferred.

The end part of $R^2$ is a methylene group which may have a substituent group, and examples of the substituent group include alkyl groups such as a methyl group.

When the central part contained in $R^2$ is the aromatic hydrocarbon group, the two end parts (the methylene group which may have a substituent group) may be present at ortho positions, meta positions, or para positions with respect to each other on the benzene ring contained in the aromatic hydrocarbon group. To exhibit the advantageous effects of the present invention, these two end parts are preferably present at meta positions or para positions with respect to each other, and more preferably at meta positions with respect to each other.

When the central part contained in $R^2$ is the alicyclic hydrocarbon group, the positional relationship of the two end parts (the methylene group which may have a substituent group) at any positions with respect to each other on the carbon ring contained in the alicyclic hydrocarbon group is not particularly limited. To exhibit the advantageous effects of the present invention, it is preferable that these two end parts are not bonded to the same carbon atom in the carbon ring, and it is more preferable that one of these two end parts are bonded to carbon atoms in the carbon ring to which the other end part is bonded, and which are separate from each other through two or more carbon atoms in the carbon ring.

The regioisomers differing in the positions of these two end parts may be used singly, or two or more kinds of such isomers may be used as a mixture.

Specifically, $R^2$ is preferably a group selected from groups represented by the following formula (4), (5), (6) or (7). In the case of the group represented by the general formula (4), the group is generally a mixture of regioisomers having the methylene groups bonded to 2,5-positions and 2,6-positions.

[Chem. 13]

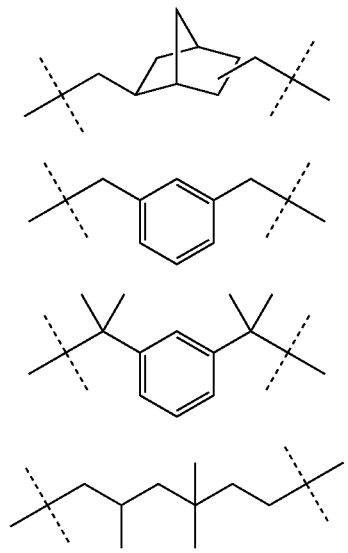

A plurality of $R^2$ may be the same as or different from each other.

In the general formula (2), each $R^3$ is independently a $C_{2-6}$ linear alkylene group or a $C_{2-6}$ linear oxyalkylene group in which a hydrogen atom may be substituted with a $C_{1-3}$ alkyl group or a (meth)acryloyloxymethylene group.

A preferred aspect of $R^3$ of the general formula (2) is a $C_{2-4}$ linear alkylene group or a $C_{2-4}$ linear oxyalkylene group in which any hydrogen atom may be substituted with a $C_{1-3}$ alkyl group.

Examples of the linear alkylene groups include —$CH_2CH_2$—, —$CH_2CH_2CH_2$—, —$CH_2CH_2CH_2CH_2$—, —$CH_2CH_2CH_2CH_2CH_2$—, and —$CH_2CH_2CH_2CH_2CH_2CH_2$—. A preferred aspect of these linear alkylene groups is, for example, —$CH_2CH_2$—, —$CH_2CH_2CH_2$—, —$CH_2CH_2CH_2CH_2$— or the like.

Examples of the linear oxyalkylene groups include —$CH_2CH_2OCH_2CH_2$—, and —$CH_2CH_2OCH_2CH_2OCH_2CH_2$—. A preferred aspect of the linear oxyalkylene group is, for example, —$CH_2CH_2OCH_2CH_2$—.

From the viewpoint that the (meth)acrylate (D) exhibits appropriate flexibility, the linear alkylene groups or the linear oxyalkylene groups each usually have 2 to 6 carbon atoms, preferably 2 to 4 carbon atoms, and more preferably 2 carbon atoms.

Examples of the alkyl groups which may substitute for hydrogen atoms contained in the linear alkylene groups or the linear oxyalkylene groups include $CH_3$—, $CH_3CH_2$—, $CH_3CH_2CH_2$—, and $(CH_3)_2CH$—. From the viewpoint that the (meth)acrylate (D) exhibits appropriate flexibility, the alkyl groups preferably have 1 to 3 carbon atoms, more preferably 1 to 2 carbon atoms, and still more preferably 1 carbon atom.

Examples of the (meth)acryloyloxymethylene groups which may substitute for hydrogen atoms contained in the linear alkylene group or the linear oxyalkylene group include a methacryloyloxymethylene group and an acryloyloxymethylene group.

A plurality of $R^3$ may be the same as or different from each other.

In the general formula (2), $R^4$ each independently represents a hydrogen atom or a methyl group. From the viewpoint of the toughness of the cured product, $R_4$ is preferably a hydrogen atom. A plurality of $R^4$ may be the same as or different from each other.

From the viewpoint of obtaining cured products having excellent toughness, it is preferable that when the (meth)acrylate (D1-1) contains three or more polymerizable groups, the polymerizable groups include a smaller number of methacryloyl groups and a larger number of acryloyl groups. It is more preferable that the polymerizable groups contain only the acryloyl groups (the (meth)acryloyloxymethylene groups which can be present as the substituents in $R^3$ are the acryloyloxymethylene groups).

The substituent in $R^3$ preferably substitutes for a hydrogen atom bonded to the carbon atom which is adjacent to the carbon atom in the linear alkylene group or the linear oxyalkylene group which is adjacent to the acryloyl group present at both end positions of the (meth)acrylate (D1-1).

The number of the alkyl groups which can substitute for hydrogen atoms and the (meth)acryloyloxymethylene groups which can substitute for hydrogen atoms is preferably 0 to 8 for each $R_3$, although not particularly limited thereto. From the viewpoint that the (meth)acrylate (D1-1) exhibits appropriate flexibility, the number of such substituents is more preferably 0 to 4, still more preferably 0 to 2, and particularly preferably 0, namely, no such substituents.

A plurality of $R^4$ may be the same as or different from each other.

In the general formula (2), X represents an oxygen atom or a sulfur atom. It is preferable that, when X is an oxygen atom in the general formula (2), the (meth)acrylate (D1-1) is a urethane urea (meth)acrylate, and X is an oxygen atom from the viewpoint of mechanical properties. A plurality of X may be the same as or different from each other.

The (meth)acrylate (D) such as the (meth)acrylate (D1-1) is preferably liquid at room temperature. The viscosity of the (meth)acrylate (D) at 65° C. is preferably 1 to 50000 mPa·s, more preferably 1 to 20000 mPa·s, and still more preferably 1 to 5000 mPa·s. When the viscosity of the (meth)acrylate (D) is in this range, the (meth)acrylate (D) exhibits a low viscosity to provide an advantage in the preparation of a dental material composition. The (meth)acrylate (D) sometimes contains minor components other than the desired (meth)acrylate (D), such as oligomers partially formed during storage at high temperatures and highly viscous byproduct compounds, and a mixture with the minor components. However, the presence of such minor components tends to be an insignificant problem in the use as a dental material composition even if these mixtures are formed as long as the viscosity is in the above-described range. The viscosity is a value measured at 65° C. with an E-type viscosimeter (for example, TVE-22H manufactured by TOKI SANGYO CO., LTD.).

The (meth)acrylates (D) may be used singly, or two or more thereof may be used as a mixture.

When the (meth)acrylate (D) such as a (meth)acrylate (D1-1) as the urethane urea type (meth)acrylate having a structure represented by the formula (1) is contained in the monomer composition of the present invention, the cured product obtained from the composition has both toughness and rigidity.

The (meth)acrylate (D) such as a (meth)acrylate (D1-1) is obtained by reacting an amine compound (A) having two or more amino groups, an iso(thio)cyanate compound (B) having two or more iso(thio)cyanato groups, and a hydroxy (meth)acrylate compound (C) having one or more polymerizable groups with one another, as described above.

For example, the (meth)acrylate (D1-1) as an example of the urethane urea type (meth)acrylate is obtained by reacting an amine compound represented by the general formula (a1') to be described, an iso(thio)cyanate compound (B) having two or more iso(thio)cyanato groups, and a hydroxy (meth) acrylate compound (C) having one or more polymerizable groups with one another.

Hereinafter, the above-described components for producing the (meth)acrylate (D) will be described in detail.

[Amine Compound (A)]

An amine compound (A) used for producing the (meth) acrylate (D) is a compound having two or more amino groups as described above. The amine compound (A) is preferably an amine compound (A') having two or three amino groups from the viewpoint of the handleability of the obtained (meth)acrylate (D).

Examples of the amine compound (A') used in order to produce the (meth)acrylate (D1-1) include an amine compound having two amino groups and represented by the following general formula (a1').

[Chem. 14]

(a1')

In the general formula (a1'), $R^1$ are as defined for $R^1$ of the general formula (2).

Suitable examples of the amine compound having two amino groups and represented by the general formula (a1') include a compound (a1) having two amino groups and represented by the general formula (a1-1) to be described later.

Examples of the amine compound (A') suitably used for production of the (meth)acrylate (D) include at least one compound selected from a compound (a1) having two amino groups and represented by the following general formula (a1-1) and a compound (a2) having three amino groups and represented by the following general formula (a2-1).

(Compound (a1))

[Chem. 15]

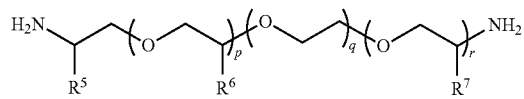

(a1-1)

In the general formula (a1-1), $R^5$ to $R^7$ each represent a hydrogen atom or a methyl group. p is an integer of 0 to 100, preferably an integer of 0 to 70, and more preferably an integer of 0 to 35. q is an integer of 0 to 100, preferably an integer of 0 to 70, and more preferably an integer of 0 to 40. r is an integer of 1 to 100, preferably an integer of 1 to 70, and more preferably an integer of 1 to 35. p+r satisfies an integer of 1 to 101, preferably an integer of 1 to 71, and more preferably an integer of 1 to 36. When a plurality of $R^6$ or $R^7$ are present, the plurality of $R^6$ or the plurality of $R^7$ may be the same as or different from each other.

The average molecular weight (MW) of the compound (a1) represented by the general formula (a1-1) is usually 100 to 4000, preferably 200 to 4000, and more preferably 400 to 2000. The average molecular weight can be confirmed by liquid chromatography mass spectrometry (LC-MS). Examples of the compound represented by the general formula (a1-1) include, but are not limited to, HK-511, ED-600, ED-900, ED-2003, D-230, D-400, D-2000, and D-4000 (trade names, manufactured by HUNTSMAN).

The compound (a1) is preferably a compound represented by the general formula (a1-1a) in which both p and q are 0 from the viewpoint of the advantageous effects of the present invention.

[Chem. 16]

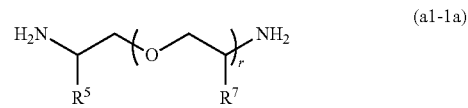

(a1-1a)

In the general formula (a1-1a), $R^5$, $R^7$, and r are as defined for $R^5$, $R^7$, and r of the general formula (1), respectively.

These compounds (a1) may be used singly, or two or more thereof may be used as a mixture.

(Compound (a2))

A compound (a2) is represented by the general formula (a2-1).

[Chem. 17]

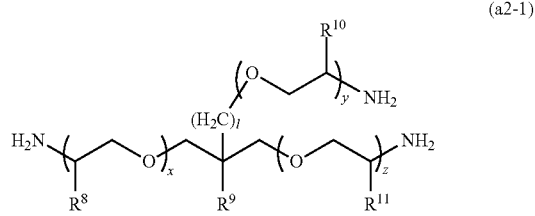

(a2-1)

In the general formula (a2-1), $R^8$, $R^{10}$, and $R^{11}$ each represent a hydrogen atom or a methyl group. $R^9$ represents a $C_{1-20}$ linear acyclic alkyl group, a $C_{3-20}$ branched acyclic alkyl group, or a $C_{3-20}$ alicyclic alkyl group. x+y+z represents an integer of 1 to 200. l represents an integer of 0 to 10. When a plurality of $R^8$, $R^{10}$, or $R^{11}$ are present, the plurality of $R^8$, the plurality of $R^{10}$, or the plurality of $R^{11}$ may be the same as or different from each other.

In the general formula (a2-1), x+y+z is usually an integer of 1 to 200, preferably an integer of 1 to 100, and more preferably an integer of 1 to 50. l is usually an integer of 0 to 10, preferably an integer of 0 to 5, and more preferably 0 or 1. The weight average molecular weight (MW) of the compound represented by the general formula (a2-1) may be usually 100 to 5000, preferably 400 to 5000, and more preferably 400 to 3000.

Examples of the $C_{1-20}$ linear acyclic alkyl group represented by $R^9$ include a methyl group, an ethyl group, a n-propyl group, a n-butyl group, a pentyl group, a hexyl group, a heptyl group, a n-octyl group, a nonyl group, a decyl group, and a dodecyl group. Examples of the $C_{3-20}$ branched acyclic alkyl group represented by $R^9$ include an isopropyl group, an isobutyl group, a t-butyl group, an isopentyl group, an isooctyl group, a 2-ethylhexyl group, 2-propylpentyl group, and an isodecyl group. Examples of the $C_{3-20}$ alicyclic alkyl group represented by $R^9$ include a cyclopropyl group, a cyclobutyl group, a cyclopentyl group, a cyclohexyl group, a cycloheptyl group, and a cyclooctyl group.

Examples of the compound represented by the general formula (a2-1) include, but are not limited to T-403, T-3000 (XTJ-509), and T-5000 (trade names, manufactured by HUNTSMAN). These compounds (a2) may be used singly, or two or more thereof may be used as a mixture. The compounds (a1) and (a2) may be used as a mixture.

The amine compounds (A) may be used singly, or two or more thereof may be used as a mixture.

[Iso(Thio)Cyanate Compound (B) Having Two or More Iso(Thio)Cyanato Groups]

The iso(thio)cyanate compound (B) used for production of the (meth)acrylate (D) is a compound having two or more iso(thio)cyanato groups as described above.

Examples of the iso(thio)cyanate compound (B) include an aliphatic polyisocyanate compound, an alicyclic polyisocyanate compound, an aromatic polyisocyanate compound, a heterocyclic polyisocyanate compound, an aliphatic polyisothiocyanate compound, an alicyclic polyisothiocyanate compound, an aromatic polyisothiocyanate compound, and a sulfur-containing heterocyclic polyisothiocyanate compound and modified products thereof. The iso(thio)cyanate compound (B) is preferably an iso(thio)cyanate compound (B') having two iso(thio)cyanato groups from the viewpoint of the handleability of the obtained (meth)acrylate (D).

More specific examples of the iso(thio)cyanate compound (B') include an aliphatic polyisocyanate compound such as pentamethylene diisocyanate, hexamethylene diisocyanate, 2,2,4-trimethylhexane diisocyanate, 2,4,4-trimethylhexamethylene diisocyanate, lysine diisocyanate methyl ester, lysine triisocyanate, m-xylylene diisocyanate, p-xylene diisocyanate, α,α,α',α'-tetramethylxylylene diisocyanate, bis(isocyanatomethyl)naphthalene, mesitylylene triisocyanate, bis(isocyanatomethyl)sulfide, bis(isocyanatoethyl)sulfide, bis(isocyanatomethyl)disulfide, bis(isocyanatoethyl)disulfide, bis(isocyanatomethylthio)methane, bis(isocyanatoethylthio)methane, bis(isocyanatoethylthio)ethane, or bis(isocyanatomethylthio)ethane; an alicyclic polyisocyanate compound such as isophorone diisocyanate, bis(isocyanatomethyl)cyclohexane, dicyclohexylmethane-4,4'-diisocyanate, cyclohexane diisocyanate, methyl cyclohexane diisocyanate, dicyclohexyl dimethylmethane isocyanate, 2,5-bis(isocyanatomethyl)bicyclo-[2.2.1]-heptane, 2,6-bis(isocyanatomethyl)bicyclo-[2.2.1]-heptane, 3,8-bis(isocyanatomethyl)tricyclodecane, 3,9-bis(isocyanatomethyl)tricyclodecane, 4,8-bis(isocyanatomethyl)tricyclodecane, or 4,9-bis(isocyanatomethyl)tricyclodecane; an aromatic polyisocyanate compound such as phenylene diisocyanate, 2,4-tolylene diisocyanate, 2,6-tolylene diisocyanate, 4,4'-diphenylmethane diisocyanate, or diphenyl sulfide-4,4-diisocyanate; and a heterocyclic polyisocyanate compound such as 2,5-diisocyanatothiophene, 2,5-bis(isocyanatomethyl)thiophene, 2,5-diisocyanatotetrahydrothiophene, 2,5-bis(isocyanatomethyl)tetrahydrothiophene, 3,4-bis(isocyanatomethyl)tetrahydrothiophene, 2,5-diisocyanato-1,4-dithiane, 2,5-bis(isocyanatomethyl)-1,4-dithiane, 4,5-diisocyanato-1,3-dithiolane, or 4,5-bis(isocyanatomethyl)-1,3-dithiolane.

Examples of the iso(thio)cyanate compound (B') include aliphatic polyisothiocyanate compounds such as hexamethylene diisothiocyanate, lysine diisothiocyanate methyl ester, lysine triisothiocyanate, m-xylylene diisothiocyanate, bis(isothiocyanatomethyl)sulfide, bis(isothiocyanatoethyl)sulfide, and bis(isothiocyanatoethyl)disulfide; alicyclic polyisothiocyanate compounds such as isophorone diisothiocyanate, bis(isothiocyanatomethyl)cyclohexane, dicyclohexylmethane diisothiocyanate, cyclohexane diisothiocyanate, methyl cyclohexane diisothiocyanate, 2,5-bis(isothiocyanatomethyl)bicyclo-[2.2.1]-heptane, 2,6-bis(isothiocyanatomethyl)bicyclo-[2.2.1]-heptane, 3,8-bis(isothiocyanatomethyl)tricyclodecane, 3,9-bis(isothiocyanatomethyl)tricyclodecane, 4,8-bis(isothiocyanatomethyl)tricyclodecane, and 4,9-bis(isothiocyanatomethyl)tricyclodecane; aromatic polyisothiocyanate compounds such as tolylene diisothiocyanate, 4,4-diphenylmethane diisothiocyanate, and diphenyl disulfide-4,4-diisothiocyanate; and sulfur-containing heterocyclic polyisothiocyanate compounds such as 2,5-diisothiocyanatothiophene, 2,5-bis(isothiocyanatomethyl)thiophene, 2,5-isothiocyanatotetrahydrothiophene, 2,5-bis(isothiocyanatomethyl)tetrahydrothiophene, 3,4-bis(isothiocyanatomethyl)tetrahydrothiophene, 2,5-diisothiocyanato-1,4-dithiane, 2,5-bis(isothiocyanatomethyl)-1,4-dithiane, 4,5-diisothiocyanato-1,3-dithiolane, and 4,5-bis(isothiocyanatomethyl)-1,3-dithiolane.

A prepolymer type modified product with a halogen substitute such as a chlorine substitute or a bromine substitute of these, an alkyl substitute, an alkoxy substitute, a nitro substitute, or polyhydric alcohol, a carbodiimide modified product, a urea modified product, a burette modified product, or a dimerization or trimerization reaction product can be used.

Of these iso(thio)cyanate compounds (B'), hexamethylene diisocyanate, 2,2,4-trimethylhexane diisocyanate, 2,4,4-trimethylhexamethylene diisocyanate, pentamethylene diisocyanate, m-xylylene diisocyanate, isophorone diisocyanate, bis(isocyanatomethyl)cyclohexane, bis(isocyanatocyclohexyl)methane, 2,5-bis(isocyanatomethyl)bicyclo-[2.2.1]-heptane, 2,6-bis(isocyanatomethyl)bicyclo-[2.2.1]-heptane, tolylene diisocyanate, phenylene diisocyanate, and 4,4'-diphenylmethane diisocyanate are preferred, and 2,2,4-trimethylhexane diisocyanate, 2,4,4-trimethylhexamethylene diisocyanate, m-xylylene diisocyanate, bis(isocyanatomethyl)cyclohexane, bis(isocyanatocyclohexyl)methane, 2,5-bis(isocyanatomethyl)bicyclo-[2.2.1]-heptane, and 2,6-bis(isocyanatomethyl)bicyclo-[2.2.1]-heptane are more preferred.

The iso(thio)cyanate compounds (B) may be used singly, or two or more thereof may be used as a mixture.

[Hydroxy (Meth)Acrylate Compound (C) Having One or More Polymerizable Groups]

The hydroxy (meth)acrylate compound (C) having one or more polymerizable groups used for production of the (meth)acrylate (D) is a compound having at least one polymerizable group selected from a methacryloyl group and an acryloyl group, and a hydroxy group as described above. The hydroxy acrylate compound having one or more polymerizable groups is preferably a hydroxy (meth)acrylate compound (C') having one polymerizable group selected from a methacryloyl group and an acryloyl group, and one hydroxy group from the viewpoint of the handleability of the obtained (meth)acrylate (D).

Examples of the hydroxy acrylate compound having one polymerizable group and one hydroxyl group suitable as the hydroxy (meth)acrylate compound (C') include 2-hydroxyethyl acrylate, 2-hydroxypropyl acrylate, 2-hydroxybutyl acrylate, 2-hydroxy-3-phenoxypropyl acrylate, 4-hydroxybutyl acrylate and 1,4-cyclohexanedimethanol monoacrylate.

Examples of the hydroxy methacrylate compound having one polymerizable group and one hydroxyl group suitable as the hydroxy (meth)acrylate compound (C') include 2-hydroxyethyl methacrylate, 2-hydroxypropyl methacrylate, 2-hydroxybutyl methacrylate, 2-hydroxy-3-phenoxypropyl methacrylate, 4-hydroxybutyl methacrylate, and 1,4-cyclohexanedimethanol monomethacrylate.

The hydroxy (meth)acrylate compounds (C) may be used singly, or two or more thereof may be used as a mixture.

The (meth)acrylate (D) of the present invention is a urethane urea type (meth)acrylate, and is obtained by reacting the amine compound (A), the iso(thio)cyanate compound (B), and the hydroxy (meth)acrylate compound (C) with one another as described above, but the reaction can be carried out by a known method or a substantially known method.

During the reaction, a catalyst may be added, or may not be added, but a catalyst is preferably added in order to enhance the reaction rate. Known catalysts accelerating the reaction between the amino group contained in the amine compound (A) and the iso(thio)cyanato group contained in the iso(thio)cyanate compound (B), and the reaction between the hydroxy group contained in the hydroxy (meth)acrylate compound (C) and the iso(thio)cyanato group contained in the iso(thio)cyanate compound (B) may be used as the catalysts.

Examples of the catalyst include organotin compounds such as dibutyltin dilaurate, dibutyltin dioctoate and tin octanoate; organic compounds of metals other than tin such as copper naphthenate, cobalt naphthenate, zinc naphthenate, acetylacetonatozirconium, acetylacetonatoiron and acetylacetonatogermanium; amine compounds and salts thereof such as triethylamine, 1,4-diazabicyclo[2.2.2]octane, 2,6,7-trimethyl-1-diazabicyclo[2.2.2]octane, 1,8-diazabicyclo[5.4.0]undecene, N,N-dimethylcyclohexylamine, pyridine, N-methylmorpholine, N,N,N',N'-tetramethylethylenediamine, N,N,N',N'-tetramethyl-1,3-butanediamine, N,N,N',N'-pentamethyldiethylenetriamine, N,N,N',N'-tetra (3-dimethylaminopropyl)-methanediamine, N,N'-dimethylpiperazine and 1,2-dimethylimidazole; and trialkylphosphine compounds such as tri-n-butylphosphine, tri-n-hexylphosphine, tricyclohexylphosphine and tri-n-octylphosphine.

Of these, dibutyltin dilaurate and tin octanoate are preferable in that the reaction is facilitated with a small amount of the catalyst and the catalyst has high selectivity for the iso(thio)cyanate compound (B). When the catalyst is used, the additive amount thereof is preferably 0.001 to 0.5% by weight, more preferably 0.002 to 0.3% by weight, still more preferably 0.01 to 0.3% by weight, yet still more preferably 0.01 to 0.2% by weight, and particularly preferably 0.05 to 0.2% by weight per 100% by weight in total of the amine compound (A), the iso(thio)cyanate compound (B), and the hydroxy (meth)acrylate compound (C). If the additive amount is below the lower limit, the catalytic effect is decreased, which may cause a significantly long reaction time. If the additive amount is above the upper limit, the catalytic effect is excessively increased, so that a large amount of reaction heat is generated, which sometimes makes it difficult to control the temperature. The catalyst may be added in the whole amount at the initiation of the reaction, or may be added successively or in portions to the reaction system as required. Such successive or portionwise addition of the catalyst prevents the generation of an excessively large amount of reaction heat at the initial stage of the reaction and thus facilitates the control of the reaction temperature.

The reaction temperature is not particularly limited, but is preferably 0 to 120° C., more preferably 20 to 100° C., and still more preferably 40 to 80° C. When the reaction is carried out at a temperature below the lower limit, the reaction rate is markedly decreased and the reaction requires a very long time to complete or may not complete in some cases. On the other hand, when the reaction is carried out at a temperature above the upper limit, side reactions may generate impurities. Such impurities sometimes cause the coloration of the (meth)acrylate (D) which is the produced urethane urea type (meth)acrylate.

From the viewpoint of stable production in the above-described preferred range of temperatures, it is preferable that the reaction temperature is controlled. The reaction between the amino group and the iso(thio)cyanato group and the reaction between the hydroxy group and the iso(thio) cyanato group are usually exothermic. When the reaction generates a large amount of heat and the temperature of the reaction product may be elevated above the preferred range of the reaction temperature, cooling is sometimes performed. When the reaction has substantially completed and the temperature of the reaction product may be decreased below the preferred range of the reaction temperature, heating is sometimes performed.

The (meth)acrylate (D) which is the urethane urea type (meth)acrylate of the present invention has polymerization activity. Thus, an unintended polymerization reaction may proceed when the system is subjected to a high temperature during the production of the (meth)acrylate (D). To prevent such unintended polymerization reaction, a known polymerization inhibitor may be added before the initiation of the reaction or during the reaction. The polymerization inhibitor is not particularly limited as long as the inhibitor can suppress the reaction of acrylate groups in production of the (meth)acrylate (D). Examples thereof include dibutylhydroxytoluene (BHT), hydroquinone (HQ), hydroquinone monomethyl ether (MEHQ) and phenothiazine (PTZ). Of these polymerization inhibitors, BHT is particularly preferable because the consumption of the inhibitor by the reaction with the isocyanato groups is small as compared to other phenolic polymerization inhibitors and also because the coloration encountered with amine polymerization inhibitors is small. The amount of the polymerization inhibitor to be added is not particularly limited, but is preferably 0.001 to 0.5% by weight, more preferably 0.002 to 0.3% by weight, still more preferably 0.005 to 0.3% by weight, yet still more preferably 0.005 to 0.1% by weight, and further preferably 0.01 to 0.1% by weight per 100 parts by weight in total of the amine compound (A), the iso(thio)cyanate compound (B), and the hydroxy (meth)acrylate compound (C). If the additive amount is below the lower limit, the polymerization inhibitor may fail to perform as expected. If the additive amount is above the upper limit, a monomer composition containing a (meth)acrylate (D) to be used, for example, a dental material composition may exhibit a markedly low curing rate to cause a limited practical applicability.

A solvent may be used in the reaction of the amine compound (A), the iso(thio)cyanate compound (B), and the hydroxy (meth)acrylate compound (C). The solvent is not particularly limited as long as the solvent does not have practical reactivity with the amine compound (A), the iso(thio)cyanate compound (B), and the hydroxy (meth)acrylate compound (C), does not inhibit the reaction, and can dissolve the raw materials and the product. The reaction may be performed without using solvents. The amine compound (A) and the hydroxy (meth)acrylate compound (C) are usually low viscous liquid and are miscible with the iso(thio)cyanate compound (B) to allow the reaction to take place without using solvents.

In the reaction of the amine compound (A), the iso(thio)cyanate compound (B), and the hydroxy (meth)acrylate compound (C), a ratio (a/b) of a number of moles of the amino groups of the amine compound (A), a, to a number of moles of the iso(thio)cyanato groups of the iso(thio)cyanate compound (B), b, is preferably 0.01 to 0.20, and more preferably 0.01 to 0.18.

A ratio ((a+c)/b) of the total number of moles (a+c) of the number of moles of the amino groups in the amine compound (A), a, and the number of moles of active hydrogen groups in the hydroxy (meth)acrylate compound (C), c, to the number of moles of the iso(thio)cyanato groups in the iso(thio)cyanate compound (B), b, is preferably 0.70 to 1.30, more preferably 0.70 to 1.20, and still more preferably 0.90 to 1.10.

By satisfying the ratio of the numbers of moles, a (meth)acrylate (D) which is a urethane urea type (meth)acrylate having excellent heat resistance, solvent resistance, and shock resistance can be more suitably obtained.

A method for admixing the amine compound (A), the iso(thio)cyanate compound (B), and the hydroxy (meth)acrylate compound (C) with one another to produce a (meth)acrylate (D) which is a urethane urea type (meth)acrylate is not particularly limited. Examples thereof include a method for adding an admixed product of an amine compound (A) and a hydroxy (meth)acrylate compound (C) to an iso(thio)cyanate compound (B) in a reaction vessel while controlling a discharged amount of the admixed product, followed by admixing the compounds to produce a (meth)acrylate (D), a method for adding an amine compound (A) to an iso(thio)cyanate compound (B) in a reaction vessel while controlling a discharged amount of the amine compound (A), followed by admixing the compounds to prepare an intermediate, and thereafter adding a hydroxy (meth)acrylate compound (C) to the intermediate while controlling a discharged amount of the hydroxy (meth)acrylate compound (C), followed by admixing the compounds to produce a (meth)acrylate (D) (a producing method by way of an intermediate), and a method for simultaneously adding an amine compound (A), an iso(thio)cyanate compound (B), and a hydroxy (meth)acrylate compound (C) to a reaction vessel while controlling discharged amounts of the compounds, followed by admixing the compounds to produce a (meth)acrylate (D). According to the producing methods due to admixing, the amount of heat generated by the reaction between the amino group and the iso(thio)cyanato group and the reaction between the hydroxy group and the iso(thio)cyanato group can be controlled in an appropriate range, and thus the temperature control during the reaction is facilitated. There can also be employed a method for adding the whole amounts of the amine compound (A), the iso(thio)cyanate compound (B), and the hydroxy (meth)acrylate compound (C) to a reaction vessel, and thereafter increasing the temperature, to react the compounds. During the reaction, the reaction temperature is sometimes sharply increased due to reaction heat and the temperature control by cooling may be appropriately required.

Of the producing methods, from the viewpoints of reactivity and pot life of the obtained (meth)acrylate (D), a producing method by way of an intermediate is preferred.

In the case of the producing method by way of an intermediate, a producing method is preferred, which includes the steps of (i) reacting an amine compound (A) and an iso(thio)cyanate compound (B) having two or more iso(thio)cyanato groups with each other to obtain an intermediate, and (ii) reacting the intermediate and a hydroxy (meth)acrylate compound (C) with each other. Hereinafter, the steps will be described.

[Step (i)]

In the step (i), a predetermined amount of the amine compound (A) is collectively added or dividedly added to the iso(thio)cyanate compound (B) for the reaction. A ratio (a/b) of the number of moles of the amino groups of the amine compound (A), a, to the number of moles of the iso(thio)cyanato groups of the iso(thio)cyanate compound (B), b, is preferably 0.01 to 0.20, and more preferably 0.01 to 0.18.

The reaction between the amine compound (A) and the iso(thio)cyanate compound (B) may be performed under presence of an additive (for example, a reaction accelerator or a stabilizer). The reaction temperature is different depending on the kinds and amounts of the compound and additive to be used, and the aspect of the produced intermediate, and is not generally limited. The reaction temperature is appropriately selected in consideration of handling properties, safety, convenience and the like.

[Step (ii)]

In the step (ii), the hydroxy (meth)acrylate compound (C) is further added to the intermediate obtained in the step (i) for the reaction. The reaction temperature is different depending on the compound to be used, and is not generally limited. The reaction temperature is appropriately selected in consideration of handling properties, safety, convenience and the like, and is preferably 90° C. or 90° C. or lower. Heating may be performed depending on the solubility of the compound to be used. The heating temperature is determined in consideration of the stability and safety of the compound.

If the amine compound (A), the iso(thio)cyanate compound (B), and the hydroxy (meth)acrylate compound (C) are collectively mixed, reaction heat is increased, which causes an unexpected side reaction between the polymerizable groups (the acryloyl groups or the methacryloyl groups), so that the polymerization reaction of the (meth)acrylate may proceed. The producing method for reacting the amine compound (A) and the iso(thio)cyanate compound (B) with each other to obtain the intermediate, and thereafter adding the hydroxy (meth)acrylate compound (C) to the intermediate tends to allow the above-described side reaction to be suppressed, whereby the (meth)acrylate (D) which is the urethane urea type (meth)acrylate can be efficiently produced.

When a (meth)acrylate (D) is produced through the steps of reacting an iso(thio)cyanate compound (B) and s hydroxy (meth)acrylate compound (C) with each other to obtain an intermediate, and thereafter reacting the obtained intermediate and an amine compound (A) with each other, an iso(thio)cyanate residue remains in the intermediate. Thus, reaction heat with the amine compound (A) is increased, which causes an unexpected side reaction between the polymerizable groups (the acryloyl groups or the methacryloyl groups), so that the polymerization reaction of the (meth)acrylate may proceed.

On the other hand, according to the producing method by way of the intermediate including the steps (i) and (ii), the amine compound (A) and the iso(thio)cyanate compound (B) are suitably reacted with each other in the mole ratio a/b of the above-described range in the step (i) to obtain the intermediate, and the amino groups of the amine compound (A) hardly remain. This tends to allow the above-described side reaction to be suppressed.

Oxygen is effective as a polymerization inhibitor for a compound containing an acryloyl group and a methacryloyl group. Thus, oxygen is sometimes introduced into the reactor to prevent unintended polymerization of the acryloyl group and the methacryloyl group during the reaction. For example, oxygen may be introduced into the reactor in such a form as dried air or oxygen gas. Preferably, oxygen is introduced into the reactor in the form of dried air. For example, the dried air may be obtained by removing water using a known drying method such as the use of a condensing air dryer. In another aspect, a mixed gas containing oxygen and an inert gas such as nitrogen may be introduced into the reactor. The aspect of such a mixed gas containing oxygen and an inert gas such as nitrogen is preferred similarly to the aspect of the dried air. The mixed gas containing oxygen and an inert gas such as nitrogen may be obtained by mixing oxygen gas or the dried air containing oxygen with a predetermined ratio of nitrogen. Nitrogen is preferably one that has been dehydrated by a known drying method. The method for the introduction is not particularly limited. For example, the gas may be continuously or intermittently introduced in the form of bubbles from the bottom of the reaction vessel. The gas may be continuously or intermittently introduced to the space at the top of the reaction vessel. The introduction amount of dry air may be appropriately set in accordance with the size and the like of the reaction container. For example, in the case of a 1-L volume reaction container, the introduction amount is usually 1 to 500 ml/min, and preferably 1 to 300 ml/min. At less than 1 ml/min, oxygen cannot be introduced in a sufficient amount and may fail to serve effectively as a polymerization inhibitor. Adding oxygen in excess of 500 ml/min increases the volatilization of the iso(thio)cyanate compound (B) during the reaction, which may result in a decrease in properties of a cured product of the (meth)acrylate (D).

If water is present as an impurity in the system during the reaction of the amine compound (A), the iso(thio)cyanate compound (B), and the hydroxy (meth)acrylate compound (C), the iso(thio)cyanate compound (B) and the water may react with each other, which may result in formation of impurities having a higher molecular weight than that of an object. An increase in the amount of impurities causes an increase in the viscosity of a product material, which is not preferred. Thus, it is preferable that as little water as possible is present in the reaction system during the reaction.

Therefore, the amount of water contained in the amine compound (A) and the hydroxy (meth)acrylate compound (C) is preferably as small as possible. Specifically, the amount of water is preferably 0.5% by weight or less, more preferably 0.3% by weight or less, and still more preferably 0.1% by weight or less based on the total amount of the amine compound (A) and the hydroxy (meth)acrylate compound (C). When the amine compound (A) and the hydroxy (meth)acrylate compound (C) contain water in an amount exceeding the upper limit, it is preferable that the compound is used as a raw material for the (meth)acrylate (D) after water is removed therefrom by a known method. The reaction vessel in which the reaction of the amine compound (A), the iso(thio)cyanate compound (B), and the hydroxy (meth)acrylate compound (C) will be performed is preferably dried by a known method to remove water therefrom.

The (meth)acrylates (D) thus produced may be for example isolated and used singly, but two or more thereof may be used as a mixture. For example, when an amine compound (A), an iso(thio)cyanate compound (B), and two or more hydroxy acrylate compounds (C) are used as raw materials to produce a (meth)acrylate (D), or when an amine compound (A), an iso(thio)cyanate compound (B), a hydroxy acrylate compound (C), and a hydroxy methacrylate compound (C) are used as raw materials to produce a (meth)acrylate (D), two or more (meth)acrylates (D) are contained.

The monomer composition of the present invention contains the (meth)acrylate (D). The monomer composition of the present invention may contain components other than the (meth)acrylate (D).

[Polymerizable Compound (E)]

The monomer composition in the present invention may further contain a polymerizable compound (E) containing at least one polymerizable group selected from a methacryloyl group and an acryloyl group (excluding a (meth)acrylate (D)) in addition to the above-described (meth)acrylate (D).

The number of the polymerizable groups contained in the polymerizable compound (E) may be 1, or may be 2 or more. The number of the polymerizable groups is preferably 2 or more and 10 or less, more preferably 2 or more and 6 or less, and still more preferably 2 or more and 4 or less.

The molecular weight of the polymerizable compound (E) is preferably 80 to 1000, and more preferably 150 to 700. If the molecular weight is below this range, the compound has a low boiling point. Thus, the above lower limit is preferred from the viewpoint of handling properties in the preparation of a monomer composition. If the molecular weight is higher than the above range, the compound tends to exhibit a high viscosity. Thus, the above upper limit is preferred from the viewpoint of handling properties in the preparation of a monomer composition such as a dental material monomer composition.

The polymerizable compound (E) is preferably liquid at room temperature. The viscosity of the polymerizable compound (E) at 65° C. is preferably 1 to 50000 mPa·s, more preferably 1 to 20000 mPa·s, still more preferably 1 to 5000 mPa·s, and particularly preferably 1 to 3000 mPa·s. When the viscosity is in this range, the monomer composition exhibits a low viscosity to provide an advantage in the use of a composition. Furthermore, the viscosity of the polymerizable compound (E) at 65° C. is more preferably lower than the viscosity of the (meth)acrylate (D) at 65° C. The polymerizable compound (E) sometimes contains minor components other than the desired polymerizable compound (E), such as oligomers partially formed during storage at high temperatures. However, the presence of such minor components tends to be an insignificant problem in the use of a monomer composition as long as the viscosity is in the above-described range. The viscosity is a value measured at 65° C. with an E type viscometer.

These polymerizable compounds (E) may be used singly, or two or more thereof may be used as a mixture.

Examples of the polymerizable compounds (E) having only one polymerizable group include polymerizable compounds represented by the following general formula (E-1).

[Chem. 18]

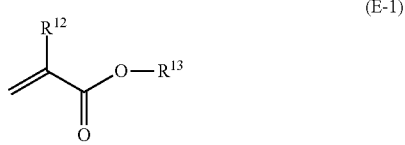

(E-1)

In the above-described general formula (E-1), $R^{12}$ is hydrogen or a methyl group, and $R^{13}$ represents a $C_{1-20}$ monovalent organic group which may contain oxygen or nitrogen.

Examples of the monovalent organic groups include hydrocarbon groups such as $C_{1-20}$ acyclic hydrocarbon groups, for example, an alkyl group, an alkenyl group, and an alkynyl group; $C_{1-20}$ cyclic hydrocarbon groups such as a cycloalkyl group, a cycloalkenyl group, a cycloalkynyl group, and an aryl group; and $C_{1-20}$ oxygen-containing hydrocarbon groups such as groups corresponding to the above hydrocarbon groups except that oxygen is introduced between at least part of the carbon atoms forming carbon-carbon bonds (but oxygen atoms are not inserted contiguously), for example, alkoxyalkyl groups, alkoxyalkylene glycol groups and tetrahydrofurfuryl groups. The $C_{1-20}$ cyclic hydrocarbon groups may have acyclic hydrocarbon moieties. The acyclic hydrocarbon moieties present in these groups may be linear or branched.

When the $C_{1-20}$ hydrocarbon groups or the $C_{1-20}$ oxygen-containing hydrocarbon groups contain linear alkylene moieties, at least one of the methylene groups in such moieties may be substituted with an ester bond, an amide bond, a carbonate bond, a urethane bond (a carbamoyl group) or a urea bond (but the methylene groups are not substituted contiguously).

Hydrogen atoms present in the organic groups such as the $C_{1-20}$ hydrocarbon group and the $C_{1-20}$ oxygen-containing hydrocarbon group may be substituted with acid groups such as carboxyl groups and phosphate groups, and functional groups such as hydroxyl groups, amino groups and epoxy groups.

Examples of the methacryloyl-containing compounds represented by the general formula (E-1) include methyl methacrylate, ethyl methacrylate, propyl methacrylate, butyl methacrylate, hexyl methacrylate, cyclohexyl methacrylate, ethoxydiethylene glycol methacrylate, methoxytriethylene glycol methacrylate, phenoxyethyl methacrylate, 2-hydroxyethyl methacrylate, 2-hydroxypropyl methacrylate, 2-hydroxybutyl methacrylate, 2-hydroxy-3-phenoxypropyl methacrylate, 4-hydroxybutyl methacrylate and 1,4-cyclohexanedimethanol monomethacrylate.

Examples of the acryloyl-containing compounds represented by the general formula (E-1) include methyl acrylate, ethyl acrylate, propyl acrylate, butyl acrylate, hexyl acrylate, cyclohexyl acrylate, ethoxydiethylene glycol acrylate, methoxytriethylene glycol acrylate, phenoxyethyl acrylate, 2-hydroxyethyl acrylate, 2-hydroxypropyl acrylate, 2-hydroxybutyl acrylate, 2-hydroxy-3-phenoxypropyl acrylate, 4-hydroxybutyl acrylate and 1,4-cyclohexanedimethanol monoacrylate.

Examples of the polymerizable compound (E) having two or more polymerizable groups include polymerizable compounds represented by the following general formula (E-2).

[Chem. 19]

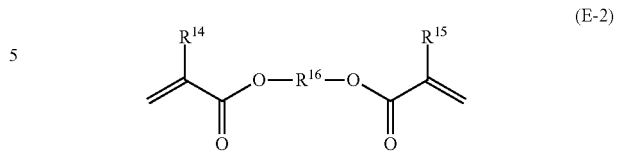

(E-2)

In the general formula (E-2), $R^{14}$ and $R^{15}$ each represent hydrogen or a methyl group and may be the same as or different from each other; and $R^{16}$ represents a $C_{1-40}$ divalent organic group which may contain oxygen or nitrogen. The (meth)acrylate (D) is not contained in the compound represented by the general formula (E-2).

Examples of the divalent organic groups include hydrocarbon groups, for example, $C_{1-40}$ acyclic hydrocarbon groups such as alkylene groups, alkenylene groups and alkynylene groups, and $C_{1-40}$ cyclic hydrocarbon groups such as cycloalkylene groups, cycloalkenylene groups, cycloalkynylene groups and arylene groups; and $C_{1-40}$ oxygen-containing hydrocarbon groups such as groups corresponding to the above hydrocarbon groups except that oxygen is introduced between at least part of the carbon atoms forming carbon-carbon bonds (but oxygen atoms are not inserted contiguously), for example, oxyalkylene groups. The $C_{1-40}$ cyclic hydrocarbon groups may have acyclic hydrocarbon moieties. The acyclic hydrocarbon moieties present in these groups may be linear or branched.

When the $C_{1-40}$ hydrocarbon groups or the $C_{1-40}$ oxygen-containing hydrocarbon groups contain linear alkylene moieties, at least one of the methylene groups in such moieties may be substituted with an ester bond, an amide bond, a carbonate bond, a urethane bond (a carbamoyl group) or a urea bond (but the methylene groups are not substituted contiguously).

Hydrogen atoms present in the organic groups such as the $C_{1-40}$ hydrocarbon groups and the $C_{1-40}$ oxygen-containing hydrocarbon groups may be substituted with acid groups such as carboxyl groups and phosphate groups, functional groups such as hydroxyl groups, amino groups and epoxy groups, and polymerizable groups such as acryloyl groups and methacryloyl groups.

Among the polymerizable compounds represented by the general formula (E-2), a suitable example of the polymerizable compounds is a polymerizable compound in which $R^{16}$ is a linear alkylene group having 2 to 20 carbon atoms, and desirably 4 to 12 carbon atoms.

Examples of the methacryloyl group-containing compounds which correspond to the above suitable polymerizable compounds include 1,4-butanediol dimethacrylate, 1,6-hexanediol dimethacrylate, 1,8-octanediol dimethacrylate, 1,9-nonanediol dimethacrylate and 1,10-decanediol dimethacrylate.

Examples of the acryloyl group-containing compounds which correspond to the above suitable polymerizable compounds include 1,4-butanediol diacrylate, 1,6-hexanediol diacrylate, 1,8-octanediol diacrylate, 1,9-nonanediol diacrylate and 1,10-decanediol diacrylate.

Among the polymerizable compounds represented by the general formula (E-2), other examples of suitable polymerizable compounds are polymerizable compounds in which $R^{16}$ is a linear oxyalkylene group having 2 to 20 carbon atoms, and desirably 4 to 12 carbon atoms.

Examples of the methacryloyl group-containing compounds which correspond to the above suitable polymerizable compounds include ethylene glycol dimethacrylate, diethylene glycol dimethacrylate, triethylene glycol dimethacrylate, tetraethylene glycol dimethacrylate, polyethylene glycol dimethacrylate, tripropylene glycol dimethacrylate, tetrapropylene glycol dimethacrylate and polypropylene glycol dimethacrylate.

Examples of the acryloyl group-containing compounds which correspond to the above suitable polymerizable compounds include ethylene glycol diacrylate, diethylene glycol diacrylate, triethylene glycol diacrylate, tetraethylene glycol diacrylate, polyethylene glycol diacrylate, tripropylene glycol diacrylate, tetrapropylene glycol diacrylate and polypropylene glycol diacrylate.

Furthermore, among the polymerizable compounds represented by the general formula (E-2), other examples of suitable polymerizable compounds are carbamoyl group-containing polymerizable compounds represented by the following general formula (E-3). The (meth)acrylate (D) is not contained in the compounds represented by the following general formula (E-3).

[Chem. 20]

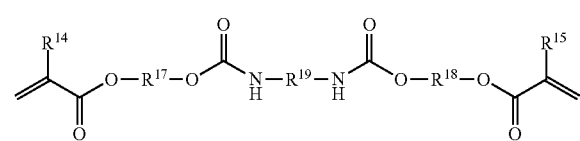

(E-3)

In the general formula (E-3), $R^{14}$ and $R^{15}$ each are hydrogen or a methyl group and may be the same as or different from each other; and $R^{17}$ and $R^{18}$ each are a $C_{1-12}$ divalent organic group which may contain oxygen, and may be the same as or different from each other.

Examples of the divalent organic groups include hydrocarbon groups, for example, $C_{1-12}$ acyclic hydrocarbon groups such as alkylene groups, and $C_{1-12}$ cyclic hydrocarbon groups such as cycloalkylene groups and arylene groups; and $C_{1-12}$ oxygen-containing hydrocarbon groups such as groups corresponding to the above hydrocarbon groups except that oxygen is introduced between at least part of the carbon atoms forming carbon-carbon bonds (but oxygen atoms are not inserted contiguously), for example, oxyalkylene groups. The $C_{1-12}$ cyclic hydrocarbon groups may have acyclic hydrocarbon moieties. The acyclic hydrocarbon moieties present in these groups may be linear or branched.

Hydrogen atoms present in the organic groups such as the $C_{1-12}$ hydrocarbon groups and the $C_{1-12}$ oxygen-containing hydrocarbon groups may be substituted with acid groups such as carboxyl groups and phosphate groups, functional groups such as hydroxyl groups, amino groups and epoxy groups, and polymerizable groups such as acryloyl groups and methacryloyl groups.

In the general formula (E-3), $R^{19}$ represents a $C_{1-20}$ divalent organic group which may contain oxygen. Examples of the divalent organic groups include hydrocarbon groups, for example, $C_{1-20}$ acyclic hydrocarbon groups such as alkylene groups; and $C_{1-20}$ oxygen-containing hydrocarbon groups such as groups corresponding to the above hydrocarbon groups except that oxygen is introduced between at least part of the carbon atoms forming carbon-carbon bonds (but oxygen atoms are not inserted contiguously), for example, oxyalkylene groups. The $C_{1-20}$ cyclic hydrocarbon groups may have acyclic hydrocarbon moieties. The acyclic hydrocarbon moieties present in these groups may be linear or branched.

Hydrogen atoms present in the organic groups such as the $C_{1-20}$ hydrocarbon groups and the $C_{1-20}$ oxygen-containing hydrocarbon groups may be substituted with acid groups such as carboxyl groups and phosphate groups, and functional groups such as hydroxyl groups, amino groups and epoxy groups.

Examples of the methacryloyl group-containing compounds represented by the general formula (E-3) include urethane methacrylates formed by the reaction between a hydroxymethacrylate such as 2-hydroxyethyl methacrylate, 2-hydroxypropyl methacrylate, 2-hydroxybutyl methacrylate, 2-hydroxy-3-phenoxypropyl methacrylate, 4-hydroxybutyl methacrylate or 1,4-cyclohexanedimethanol monomethacrylate, and a diisocyanate such as 2,4- or 2,6-toluene diisocyanate, 4,4'-, 2,4'- or 2,2'-diphenylmethane-diisocyanate, 1,6-hexamethylene diisocyanate, or 2,2,4- or 2,4,4-trimethyl-1,6-hexamethylene-diisocyanate. Examples of such urethane methacrylates include 2,2,4-trimethylhexamethylene bis(2-carbamoyloxyethyl) dimethacrylate (UDMA).

Examples of the acryloyl group-containing compounds represented by the general formula (E-3) include urethane acrylates formed by the reaction between a hydroxyacrylate such as 2-hydroxyethyl acrylate, 2-hydroxypropyl acrylate, 2-hydroxybutyl acrylate, 2-hydroxy-3-phenoxypropyl acrylate, 4-hydroxybutyl acrylate or 1,4-cyclohexanedimethanol monoacrylate, and a diisocyanate such as 2,4- or 2,6-toluene diisocyanate, 4,4'-, 2,4'- or 2,2'-diphenylmethane-diisocyanate, 1,6-hexamethylene diisocyanate, or 2,2,4- or 2,4,4-trimethyl-1,6-hexamethylene-diisocyanate. Examples of such urethane acrylates include 2,2,4-trimethylhexamethylene bis(2-carbamoyloxyethyl) diacrylate.

Another preferred examples of the polymerizable compound represented by the general formula (E-2) include polymerizable compounds represented by the following general formula (E-4).

[Chem. 21]

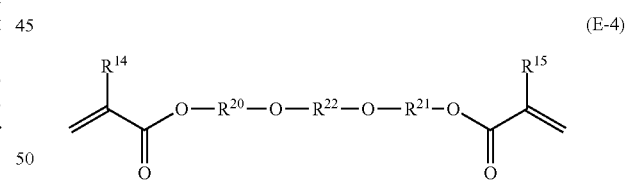

(E-4)

In the general formula (E-4), $R^{14}$ and $R^{15}$ each represent hydrogen or a methyl group and may be the same as or different from each other; and $R^{20}$ and $R^{21}$ each represent a $C_{1-12}$ divalent organic group which may contain oxygen, and may be the same as or different from each other.

Examples of the divalent organic groups include hydrocarbon groups, for example, $C_{1-12}$ acyclic hydrocarbon groups such as alkylene groups, and $C_{1-12}$ cyclic hydrocarbon groups such as cycloalkylene groups and arylene groups; and $C_{1-12}$ oxygen-containing hydrocarbon groups such as groups corresponding to the above hydrocarbon groups except that oxygen is introduced between at least part of the carbon atoms forming carbon-carbon bonds (but oxygen atoms are not inserted contiguously), for example, oxyalkylene groups. The $C_{1-12}$ cyclic hydrocarbon groups may have acyclic hydrocarbon moieties. The acyclic hydrocarbon moieties present in these groups may be linear or branched.

Hydrogen atoms present in the organic groups such as the $C_{1-12}$ hydrocarbon groups and the $C_{1-12}$ oxygen-containing hydrocarbon groups may be substituted with acid groups such as carboxyl groups and phosphate groups, functional groups such as hydroxyl groups, amino groups and epoxy groups, and polymerizable groups such as acryloyl groups and methacryloyl groups.

In the general formula (E-4), $R^{22}$ represents a $C_{1-20}$ divalent organic group which may contain oxygen.

Examples of the divalent organic groups include $C_{1-20}$ hydrocarbon groups such as alkylene groups, cycloalkylene groups and arylene groups; and $C_{1-20}$ oxygen-containing hydrocarbon groups such as groups corresponding to the above hydrocarbon groups except that oxygen is introduced between at least part of the carbon atoms forming carbon-carbon bonds (but oxygen atoms are not inserted contiguously), for example, oxyalkylene groups. The $C_{1-20}$ cyclic hydrocarbon groups may have acyclic hydrocarbon moieties.

Hydrogen atoms present in the organic groups such as the $C_{1-20}$ hydrocarbon groups and the $C_{1-20}$ oxygen-containing hydrocarbon groups may be substituted with acid groups such as carboxyl groups and phosphate groups, and functional groups such as hydroxyl groups, amino groups and epoxy groups.

Examples of the methacryloyl group-containing compounds represented by the general formula (E-4) include 2,2-bis[4-(3-methacryloyloxy-2-hydroxypropoxy)phenyl] propane (Bis-GMA), ethylene oxide-modified bisphenol A dimethacrylate and propylene oxide-modified bisphenol A dimethacrylate.

Examples of the acryloyl group-containing compounds represented by the general formula (E-4) include 2,2-bis[4-(3-acryloyloxy-2-hydroxypropoxy)phenyl]propane, ethylene oxide-modified bisphenol A diacrylate and propylene oxide-modified bisphenol A diacrylate.

When the monomer composition of the present invention is used in such an application as dental adhesive materials, it is preferable that the monomer composition contain, as the polymerizable compound (E), a polymerizable compound exhibiting a bonding function. Examples of the polymerizable compound (E) exhibiting a bonding function include polymerizable compounds having at least one polymerizable group selected from methacryloyl groups and acryloyl groups, and an acidic group. Examples of the acidic groups include phosphate residues, pyrophosphate residues, thiophosphate residues, carboxylate residues and sulfonate residues.

Examples of the polymerizable compounds having a methacryloyl group and a phosphate residue include 2-methacryloyloxyethyl dihydrogen phosphate, 9-methacryloyloxynonyl dihydrogen phosphate, 10-methacryloyloxydecyl dihydrogen phosphate, 11-methacryloyloxyundecyl dihydrogen phosphate, 20-methacryloyloxyeicosyl dihydrogen phosphate, 1,3-dimethacryloyloxypropyl-2-dihydrogen phosphate, 2-methacryloyloxyethyl phenyl phosphoric acid, 2-methacryloyloxyethyl 2'-bromoethyl phosphoric acid, methacryloyloxyethyl phenyl phosphonate, and acid chlorides of these compounds.

Examples of the polymerizable compounds having an acryloyl group and a phosphate residue include 2-acryloyloxyethyl dihydrogen phosphate, 9-acryloyloxynonyl dihydrogen phosphate, 10-acryloyloxydecyl dihydrogen phosphate, 11-acryloyloxyundecyl dihydrogen phosphate, 20-acryloyloxyeicosyl dihydrogen phosphate, 1,3-diacryloyloxypropyl-2-dihydrogen phosphate, 2-acryloyloxyethyl phenyl phosphoric acid, 2-acryloyloxyethyl 2'-bromoethyl phosphoric acid, acryloyloxyethyl phenyl phosphonate, and acid chlorides of these compounds.

Examples of the polymerizable compounds having a methacryloyl group and a pyrophosphate residue include di(2-methacryloyloxyethyl) pyrophosphate, and acid chlorides thereof.

Examples of the polymerizable compounds having an acryloyl group and a pyrophosphate residue include di(2-acryloyloxyethyl) pyrophosphate, and acid chlorides thereof.

Examples of the polymerizable compounds having a methacryloyl group and a thiophosphate residue include 2-methacryloyloxyethyl dihydrogen dithiophosphate, 10-methacryloyloxydecyl dihydrogen thiophosphate, and acid chlorides of these compounds.

Examples of the polymerizable compounds having an acryloyl group and a thiophosphate residue include 2-acryloyloxyethyl dihydrogen dithiophosphate, 10-acryloyloxydecyl dihydrogen thiophosphate, and acid chlorides of these compounds.

Examples of the polymerizable compounds having a methacryloyl group and a carboxylate residue include 4-methacryloyloxyethoxycarbonylphthalic acid, 5-methacryloylaminopentylcarboxylic acid, 11-methacryloyloxy-1,1-undecanedicarboxylic acid, and acid chlorides and acid anhydrides of these compounds.

Examples of the polymerizable compounds having an acryloyl group and a carboxylate residue include 4-acryloyloxyethoxycarbonylphthalic acid, 5-acryloylaminopentylcarboxylic acid, 11-acryloyloxy-1,1-undecanedicarboxylic acid, and acid chlorides and acid anhydrides of these compounds.

Examples of the polymerizable compounds having a methacryloyl group and a sulfonate residue include 2-sulfoethyl methacrylate and 2-methacrylamido-2-methylpropanesulfonic acid.

Examples of the polymerizable compounds having an acryloyl group and a sulfonate residue include 2-sulfoethyl acrylate and 2-acrylamido-2-methylpropanesulfonic acid.

The monomer composition of the present invention may contain an acidic group-containing polymerizable compound which is not categorized into the polymerizable compounds (E).

Examples of such acidic group-containing polymerizable compounds include sulfonate residue-containing polymerizable compounds such as styrenesulfonic acid. The acidic group-containing polymerizable compounds may be used singly, or two or more may be used in combination.

When the monomer composition of the present invention contains such an acidic group-containing polymerizable compound, the amount of the acidic group-containing polymerizable compound to be added is not particularly limited. Usually, the monomer composition contains the acidic group-containing polymerizable compound in such an amount that the number of the polymerizable groups present in the acidic group-containing polymerizable compound is 50% or less relative to the total number of the polymerizable groups in the monomer composition.

The amount of the (meth)acrylate (D) in 100% by weight of the monomer composition of the present invention is different depending on the applications and the like, and can be appropriately set. The amount of the (meth)acrylate (D) is usually 50 to 100% by weight, and preferably 60 to 90% by weight. The amount of the polymerizable compound (E)

in 100% by weight of the monomer composition of the present invention is usually 0 to 60% by weight, and preferably 10 to 40% by weight.

The viscosity of the monomer composition of the present invention is not particularly limited, but is preferably in the range of 1 to 100,000 mPa·s at 65° C., more preferably in the range of 5 to 60,000 mPa·s, still more preferably in the range of 10 to 30,000 mPa·s, and yet still more preferably in the range of 100 to 10,000 mPa·s. If the viscosity is above the upper limit, when a component such as a filler is added to the monomer composition to produce the dental material composition of the present invention, the dispersibility thereof becomes poor, which may make it difficult to obtain a uniform mixture. If, on the other hand, the viscosity is less than the lower limit, when a component such as a filler is mixed to the monomer composition to produce the dental material composition of the present invention, an increased amount of air bubbles enter the composition, which may make it difficult to obtain a uniform mixture. The monomer composition is sometimes partially oligomerized during storage at high temperatures. The viscosity is a value immediately after the production of the monomer composition before the occurrence of any oligomerization.

The hue of the monomer composition in the present invention is not particularly limited, but is preferably suited for use as a raw material for dental materials. Specifically, the APHA scale is preferably 500 or less, more preferably 200 or less, and still more preferably 100 or less.

In the production of the monomer composition of the present invention, a method in which the (meth)acrylate (D) and the polymerizable compound (E) are mixed together is not particularly limited. For example, the monomer composition of the present invention is obtained by adding the (meth)acrylate (D) and the polymerizable compound (E) into a container and stirring the mixture to uniformity while performing heating appropriately.

In order to provide an enhancement in storage stability, the monomer composition of the present invention may contain the polymerization inhibitor described above. The inhibitor may be added during the synthesis of the (meth) acrylate (D) as described above, or may be added during a downstream step as required.

The monomer composition of the present invention has room-temperature polymerizability, thermal polymerizability or photopolymerizability when a polymerization initiator to be described later is added thereto. A molded body (cured product) is obtained by curing the monomer composition. The cured product of the molded body (cured product) obtained by curing the monomer composition of the present invention has high mechanical properties as compared with the molded body (cured product) obtained by curing the conventional monomer composition, and particularly has both high breaking strength and high breaking energy in a balanced manner. In other words, the cured product is a material having both toughness and rigidity.

The monomer composition of the present invention may contain additives such as a bactericidal agent, a disinfectant, a stabilizer, and a preserving agent as required as long as the advantageous effects of the present invention are not impaired.

The monomer composition of the present invention has the above-described properties, and is suitable as the dental material monomer composition.

[Dental Material Composition]

The monomer composition of the present invention can be suitably used as components of the dental material composition of the present invention, and the dental material composition contains the above-described monomer composition, polymerization initiator, filler and the like. The dental material composition has room-temperature polymerizability, thermal polymerizability, or photopolymerizability, and can be suitably used as dental restorative materials, for example.

The amount of the monomer composition to be added is usually in the range of 20 to 80% by weight, and preferably in the range of 20 to 50% by weight per 100% by weight of the dental material composition.

The polymerization initiator to be used may be any of general polymerization initiators used in the dental field, and is usually selected in consideration of the polymerizability of the polymerizable compounds contained in the dental material composition, and the polymerization conditions.

In the case of room-temperature polymerization, for example, a redox polymerization initiator which is a combination of an oxidant and a reductant is suitable. When using a redox polymerization initiator, an oxidant and a reductant which are separately packaged need to be mixed with each other immediately before use.

The oxidants are not particularly limited. Examples thereof include organic peroxides such as diacyl peroxides, peroxy esters, dialkyl peroxides, peroxyketals, ketone peroxides and hydroperoxides. Examples of the organic peroxides include diacyl peroxides such as benzoyl peroxide, 2,4-dichlorobenzoyl peroxide and m-toluoyl peroxide; peroxy esters such as t-butyl peroxybenzoate, bis-t-butyl peroxyisophthalate, 2,5-dimethyl-2,5-bis(benzoylperoxy) hexane, t-butyl peroxy-2-ethylhexanoate and t-butyl peroxyisopropyl carbonate; dialkyl peroxides such as dicumyl peroxide, di-t-butyl peroxide and lauroyl peroxide; peroxyketals such as 1,1-bis(t-butylperoxy)-3,3,5-trimethyl-cyclohexane; ketone peroxides such as methyl ethyl ketone peroxide; and hydroperoxides such as t-butyl hydroperoxide.

The reductants are not particularly limited, but tertiary amines are usually used. Examples of the tertiary amines include N,N-dimethylaniline, N,N-dimethyl-p-toluidine, N,N-dimethyl-m-toluidine, N,N-diethyl-p-toluidine, N,N-dimethyl-3,5-dimethylaniline, N,N-dimethyl-3,4-dimethyl-aniline, N,N-dimethyl-4-ethylaniline, N,N-dimethyl-4-i-propylaniline, N,N-dimethyl-4-t-butylaniline, N,N-dimethyl-3,5-di-t-butylaniline, N,N-bis(2-hydroxyethyl)-p-toluidine, N,N-bis(2-hydroxyethyl)-3,5-dimethylaniline, N,N-bis(2-hydroxyethyl)-3,4-dimethylaniline, N,N-bis(2-hydroxyethyl)-4-ethylaniline, N,N-bis(2-hydroxyethyl)-4-i-propylaniline, N,N-bis(2-hydroxyethyl)-4-t-butylaniline, N,N-di(2-hydroxyethyl)-3,5-di-i-propylaniline, N,N-bis(2-hydroxyethyl)-3,5-di-t-butylaniline, ethyl 4-dimethylamino-benzoate, n-butoxyethyl 4-dimethylaminobenzoate, (2-methacryloyloxy)ethyl 4-dimethylaminobenzoate, trimethylamine, triethylamine, N-methyldiethanolamine, N-ethyldiethanolamine, N-n-butyldiethanolamine, N-lauryldiethanolamine, triethanolamine, (2-dimethylamino)ethyl methacrylate, N,N-bis(methacryloyloxyethyl)-N-methylamine, N,N-bis(methacryloyloxyethyl)-N-ethylamine, N,N-bis(2-hydroxyethyl)-N-methacryloyloxyethylamine, N,N-bis(methacryloyloxyethyl)-N-(2-hydroxyethyl)amine and tris(methacryloyloxyethyl)amine.

Besides these organic peroxide/amine systems, redox polymerization initiators such as cumene hydroperoxide/thiourea systems, ascorbic acid/$Cu^{2+}$ salt systems and organic peroxide/amine/sulfinic acid (or sulfinate salt) systems may be used. Polymerization initiators such as tributyl borane and organic sulfinic acids are also suitably used.

In the case of thermal polymerization with heating, it is preferable to use peroxides or azo compounds.

The peroxides are not particularly limited, and examples thereof include benzoyl peroxide, t-butyl hydroperoxide and cumene hydroperoxide. The azo compounds are not particularly limited, and examples thereof include azobisisobutyronitrile.

In the case of photopolymerization with the irradiation of visible lights, preferred initiators are redox initiators such as α-diketones/tertiary amines, α-diketones/aldehydes and α-diketones/mercaptans.

Examples of the photopolymerization initiators include, but are not particularly limited to, α-diketones/reductants, ketals/reductants and thioxanthones/reductants. Examples of the α-diketones include camphorquinone, benzil and 2,3-pentanedione. Examples of the ketals include benzyl dimethyl ketal and benzyl diethyl ketal. Examples of the thioxanthones include 2-chlorothioxanthone and 2,4-diethylthioxanthone. Examples of the reductants include tertiary amines such as Michler's ketone, 2-(dimethylamino) ethyl methacrylate, N,N-bis[(meth)acryloyloxyethyl]-N-methylamine, ethyl N,N-dimethylaminobenzoate, butyl 4-dimethylaminobenzoate, butoxyethyl 4-dimethylaminobenzoate, N-methyldiethanolamine, 4-dimethylaminobenzophenone, N,N-bis(2-hydroxyethyl)-p-toluidine and dimethylaminophenanthrol; aldehydes such as citronellal, lauryl aldehyde, phthalic dialdehyde, dimethylaminobenzaldehyde and terephthalaldehyde; and thiol group-containing compounds such as 2-mercaptobenzoxazole, decanethiol, 3-mercaptopropyltrimethoxysilane, 4-mercaptoacetophenone, thiosalicylic acid and thiobenzoic acid. α-diketone/organic peroxide/reductant systems obtained by adding organic peroxides to these redox systems are suitably used.

In the case of photopolymerization with the irradiation of UV lights, suitable initiators are benzoin alkyl ethers and benzyl dimethyl ketal. Photopolymerization initiators such as (bis)acylphosphine oxides are also suitably used.

Of the (bis)acylphosphine oxides, examples of the acylphosphine oxides include 2,4,6-trimethylbenzoyldiphenylphosphine oxide, 2,6-dimethoxybenzoyldiphenylphosphine oxide, 2,6-dichlorobenzoyldiphenylphosphine oxide, 2,4,6-trimethylbenzoylmethoxyphenylphosphine oxide, 2,4,6-trimethylbenzoylethoxyphenylphosphine oxide, 2,3,5,6-tetramethylbenzoyldiphenylphosphine oxide and benzoyldi-(2,6-dimethylphenyl)phosphonate. Examples of the bisacylphosphine oxides include bis-(2,6-dichlorobenzoyl)phenylphosphine oxide, bis-(2,6-dichlorobenzoyl)-2,5-dimethylphenylphosphine oxide, bis-(2,6-dichlorobenzoyl)-4-propylphenylphosphine oxide, bis-(2,6-dichlorobenzoyl)-1-naphthylphosphine oxide, bis-(2,6-dimethoxybenzoyl) phenylphosphine oxide, bis-(2,6-dimethoxybenzoyl)-2,4,4-trimethylpentylphosphine oxide, bis-(2,6-dimethoxybenzoyl)-2,5-dimethylphenylphosphine oxide, bis-(2,4,6-trimethylbenzoyl)phenylphosphine oxide and (2,5,6-trimethylbenzoyl)-2,4,4-trimethylpentylphosphine oxide. These (bis)acylphosphine oxide photopolymerization initiators may be used singly or in combination with various reductants such as amines, aldehydes, mercaptans and sulfinate salts. These reductants may be suitably used also in combination with the visible light photopolymerization initiators.

The polymerization initiators may be used singly, or two or more thereof may be used as a mixture. The amount of the polymerization initiator to be added is usually in the range of 0.01 to 20% by weight, and preferably 0.1 to 5% by weight per 100% by weight of the dental material composition.

The filler to be used may be any of general fillers used in the dental field. The fillers are usually broadly categorized into organic fillers and inorganic fillers.

Examples of the organic fillers include fine powders of polymethyl methacrylate, polyethyl methacrylate, methyl methacrylate-ethyl methacrylate copolymer, crosslinked polymethyl methacrylate, crosslinked polyethyl methacrylate, ethylene-vinyl acetate copolymer and styrene-butadiene copolymer.

Examples of the inorganic fillers include fine powders of various glasses (based on silicon dioxide and optionally containing oxides of, for example, heavy metals, boron and aluminum), various ceramics, diatomaceous earth, kaolin, clay minerals (such as montmorillonite), activated clay, synthetic zeolite, mica, calcium fluoride, ytterbium fluoride, calcium phosphate, barium sulfate, zirconium dioxide, titanium dioxide and hydroxyapatite. Specific examples of the inorganic fillers include barium borosilicate glasses (such as Kimble Raysorb T3000, Schott 8235, Schott GM27884 and Schott GM39923), strontium boroaluminosilicate glasses (such as Raysorb T4000, Schott G018-093 and Schott GM32087), lanthanum glasses (such as Schott GM31684), fluoroaluminosilicate glasses (such as Schott G018-091 and Schott G018-117), and boroaluminosilicate glasses containing zirconium and/or cesium (such as Schott G018-307, G018-308 and G018-310).

An organic inorganic composite filler may be used which is obtained by adding a polymerizable compound beforehand to the inorganic filler to provide a paste, which is then cured by polymerization and crushed.

In an aspect of the dental material composition, the composition containing a microfiller having a particle diameter of 0.1 μm or less is suitable as a dental composite resin. Preferred examples of the materials for fillers having a small particle diameter include silica (for example, product name: AEROSIL), alumina, zirconia and titania. The addition of such an inorganic filler having a small particle diameter is advantageous in order for a cured product of the composite resin to achieve high polishing smoothness.

These fillers may be surface treated with agents such as silane coupling agents in accordance with purposes. Examples of such surface treating agents to be used include known silane coupling agents, for example, organosilicon compounds such as γ-methacryloxyalkyltrimethoxysilanes (the number of carbon atoms between the methacryloxy group and the silicon atom: 3 to 12), γ-methacryloxyalkyltriethoxysilanes (the number of carbon atoms between the methacryloxy group and the silicon atom: 3 to 12), vinyltrimethoxysilane, vinylethoxysilane and vinyltriacetoxysilane. The concentration of the surface treating agent is usually in the range of 0.1 to 20% by weight, and preferably 1 to 10% by weight per 100% by weight of the filler.

The fillers may be used singly, or two or more thereof may be used as a mixture. The amount of the filler to be added may be determined appropriately in consideration of handling properties (viscosity) of the dental material composition (for example, the composite resin paste) and mechanical properties of cured products of the paste. The amount is usually 10 to 2000 parts by weight, preferably 50 to 1000 parts by weight, and more preferably 100 to 600 parts by weight per 100 parts by weight of all the components contained in the dental material composition except the filler.

The dental material composition of the present invention may appropriately contain components other than the monomer composition of the present invention, the polymerization initiator and the filler in accordance with the purpose.

For example, the dental material composition may contain the above-described polymerization inhibitor for enhancing storage stability. To adjust the color tone, the dental material composition may contain known colorants such as pigments and dyes. Furthermore, the dental material composition may contain known reinforcing materials such as fibers to increase the strength of cured products.

The dental material composition of the present invention may be cured under appropriate conditions in accordance with the polymerization method of the above-described polymerization initiator. In the case where, for example, the dental material composition of the present invention contains a visible light photopolymerization initiator, a desired cured product may be obtained by shaping the dental material composition into a predetermined form, and then irradiating the dental material composition with visible light for a predetermined time using a known light irradiator. The conditions such as irradiation intensity and irradiation intensity may be changed appropriately in accordance with the curability of the dental material composition. The cured product which has been cured by the irradiation of light such as visible light may be heat treated under more appropriate conditions, and thereby the mechanical properties of the cured product can be enhanced.

The dental material of the present invention is obtained by, for example, a method for producing a dental material including the steps of: injecting the above-described dental material composition into a casting mold; and curing the dental material composition in the casting mold.

The cured product of the dental material composition of the present invention which is obtained as described above may be suitably used as the dental material.

The use method of the dental material composition of the present invention is not particularly limited as long as it is generally known as the use method of the dental material. When, for example, the dental material composition of the present invention is used as a composite resin for filling carious cavities, the purpose may be fulfilled by filling a cavity in the mouth with the dental material composition and photocuring the composition using a known light irradiator. When used as a crowning composite resin, the composition may be shaped into an appropriate form, photocured using a known light irradiator and heat treated under predetermined conditions to obtain a desired crown material.

The cured product of the dental material composition of the present invention including the monomer composition of the present invention has high mechanical properties as compared to cured products of conventional dental material compositions containing conventional monomer compositions, and in particular exhibit high flexural breaking strength. The detailed reasons as to why the cured products of the dental material compositions of the present invention have high mechanical properties are not fully understood. In the case of the dental material composition or in particular a composite resin as a typical example, the major proportion of the weight of the composition is accounted for by the monomer composition and the filler, and therefore these two components have a very high influence on the mechanical properties of the composite resin cured products. When the properties of an inorganic filler are compared with the properties of a cured product of the monomer composition, in general, the inorganic filler has a far higher strength than that of the cured product of the monomer composition. In contrast, the cured product of the monomer composition of the present invention has excellent flexibility. Thus, in the composite resin cured product, the inorganic filler may be considered as a hard segment component and the cured product as a soft segment component. In such a system, a blind increase in the rigidity of the soft segment component does not lead to an enhancement in the mechanical properties of the composite resin cured product or rather sometimes results in a hard but brittle material. As far as the soft segment component is concerned, it is considered that an increase in the toughness thereof while maintaining a certain level of rigidity will contribute to an enhancement in the mechanical properties of the composite resin cured product. When cured, the monomer composition of the present invention preferably contains a specific amount of the (meth) acrylate (D) having a specific structure to provide a material having both toughness and rigidity. It is presumed that such a cured product is suitable as the soft segment component in the composite resin cured product, and has high mechanical properties and, in particular, will exhibit high flexural breaking strength.

The dental material composition in the present invention may be suitably used as a dental material. Examples of such materials include dental restorative materials, denture base resins, denture base liners, impression materials, luting materials (resin cements, resin-modified glass ionomer cements), dental bonding materials (orthodontic bonding materials, cavity-coating bonding materials), dental fissure sealants, CAD/CAM resin blocks, temporary crowns and artificial tooth materials.

The dental material composition of the present invention may be preferably used also as a dental restorative material. The dental restorative materials are classified by application into categories such as dental crown composite resins, composite resins for filling carious cavities, composite resins for making dental abutments, and composite resins for filling restoration. The cured product of the dental material composition of the present invention exhibits high mechanical properties, and may be particularly preferably used as the dental crown composite resins.

EXAMPLES

Hereinafter, the present invention will be more specifically described based on Examples without limiting the scope of the present invention to such Examples.

The abbreviations of compounds used in Examples of the present invention will be shown below.

EBADMA (2.6): ethoxylated bisphenol A dimethacrylate (2.6EO modified)

UDMA: (2,2,4-trimethylhexamethylenebis(2-carbamoyloxyethyl)dimethacrylate) (manufactured by SARTOMER Company, Inc.)

HEA: 2-hydroxyethyl acrylate

HPA: 2-hydroxypropyl acrylate

HEMA: 2-hydroxyethyl methacrylate

NBDI: mixture of 2,5-bis(isocyanatomethyl)bicyclo[2.2.1]heptane and 2,6-bis(isocyanatomethyl)bicyclo[2.2.1]heptane XDI: m-xylylene diisocyanate TMXDI: 1,3-tetramethyl xylylene diisocyanate TMHDI: mixture of 2,2,4-trimethyl hexamethylene diisocyanate and 2,4,4-trimethyl hexamethylene diisocyanate ED-600: poly(propylene glycol)blockpoly(ethylene glycol)blockpoly(propylene glycol)bis(2-aminopropylether) having a weight average molecular weight of 600

DBTDL: dibutyltin dilaurate

BHT: dibutylhydroxytoluene

CQ: camphorquinone

DMAB2-BE: 2-butoxyethyl 4-(dimethylamino)benzoate

[Method of Bending Test]

The bending test method in Examples and Comparative Examples of the present invention will be described below.

(Fabrication of Bending Test Pieces Including Cured Bodies Containing Monomer Compositions or Dental Material Monomer Compositions)

0.5 parts by weight of CQ and 0.5 parts by weight of DMAB2-BE were added into 10 parts by weight of a monomer composition from any of Examples and Comparative Examples. The mixture was stirred to uniformity at room temperature. Furthermore, to the solution, 15 parts by weight of silica glass (Fuselex-X (TATSUMORI LTD.)) was added. The mixture was stirred to uniformity using a mortar, followed by defoaming to prepare a composition (dental material composition). The obtained composition (dental material composition) was added into a 2×2×25 mm stainless steel mold and was irradiated with light using a visible light irradiator (Solidilite V manufactured by SHOFU INC.) for 3 minutes on each side, namely, for a total of 6 minutes on both sides. Furthermore, the test piece was removed from the mold and was heat treated in an oven at 130° C. for 2 hours. The test piece was removed from the oven and was cooled to room temperature. Thereafter, the test piece was soaked in distilled water in a closable sample bottle and was stored at 37° C. for 24 hours. The test piece thus obtained was used.

(Bending Test)

The test pieces fabricated in the above manners were subjected to a three-point bending test using a tester (AUTOGRAPH EZ-S manufactured by Shimadzu Corporation) under conditions in which a distance between supporting points was 20 mm and a cross head speed was 1 mm/min.

[Measuring Method of Viscosity]

In Examples and Comparative Examples of the present invention, the viscosity was measured using an E type viscometer (TVE-22H manufactured by TOKI SANGYO CO., LTD.). The temperature was controlled at 65° C. using a circulation thermostatic tank.

[Measuring Method of Refractive Index]

In Examples and Comparative Examples of the present invention, the refractive index was measured using an Abbe type full digital refractive index system (Abbemat 550 manufactured by AntonPaar). The temperature was controlled at 25° C.

[Measuring Method of IR Spectrum]

The IR spectrum (infrared absorption spectrum) of the reaction product containing the (meth)acrylate (A-1) obtained in each of Examples was measured using a Fourier transform infrared spectroscopic analyzer Spectrum Two/UATR (Universal Attenuated Total Reflectance) manufactured by PerkinElmer Japan Co., Ltd.

The monomer composition obtained in each of Examples was allowed to stand at 20° C. for 24 hours, and the IR spectrum was then measured at 20° C.

Example 1

22.94 parts by weight of NBDI and 2.00 parts by weight of ED-600 were added dropwise into a thoroughly dried 100-mL four-necked flask equipped with a stirring blade and a thermometer, followed by reacting at 60° C. for 3 hours, to obtain a solution containing an intermediate. The obtained solution containing an intermediate was heated to 90° C. To the solution, 0.1 parts by weight of DBTDL and 0.05 parts by weight of BHT were added, followed by dissolving to obtain a homogeneous solution. Furthermore, 25.06 parts by weight of HEA was added dropwise into the solution over a period of 1 hour. The dropwise addition was accompanied by an increase in inside temperature due to the reaction heat, and thus the amount of the dropwise addition was controlled so that the temperature did not exceed 90° C. After the whole amount had been added dropwise, the reaction was performed for 10 hours while the reaction temperature was kept at 90° C. During this process, the progress of the reaction was tracked by HPLC analysis to confirm the end point of the reaction. The product was discharged from the reactor. In this manner, 50 g of a composition containing a urethane urea acrylate (D-1) (urethane urea type (meth)acrylate (D-1)) was obtained. The composition had a viscosity of 1330 mPa·s at 65° C. The composition had a refractive index of 1.5051 at 25° C.

12.0 parts by weight of the obtained composition containing a urethane urea acrylate (D-1) and 3.0 parts by weight of EBADMA (2.6) were added into a container. The mixture was stirred to uniformity at 50° C. to obtain a monomer composition (dental material monomer composition) (1).

0.012 parts by weight of CQ and 0.012 parts by weight of DMAB2-BE were added into 2.4 parts by weight of the obtained monomer composition (1). The mixture was stirred to uniformity at room temperature. Furthermore, to the solution, 3.6 parts by weight of silica glass was added to obtain a dental material composition (1). When a cured product of the dental material composition (1) was subjected to a bending test, the cured product had elastic modulus of 8.0 GPa, breaking strength of 203 MPa, and breaking energy of 49 mJ.

Example 2

The same reaction as that of Example 1 was performed except that the amounts of NBDI, ED-600, and HEA to be added were changed to amounts described in Table 1, to obtain 50 g of a composition containing a urethane urea acrylate (D-2) (urethane urea type (meth)acrylate (D-2)). The composition had a viscosity of 1440 mPa·s at 65° C. The composition had a refractive index of 1.5047 at 25° C.

24.0 parts by weight of the obtained composition containing a urethane urea acrylate (D-2) and 6.0 parts by weight of EBADMA (2.6) were added into a container. The mixture was stirred to uniformity at 50° C. to obtain a monomer composition (dental material monomer composition) (2).

CQ and DMAB2-BE were added in the same manner as in Example 1 except that a monomer composition (1) was changed to the monomer composition (2). Furthermore, to the mixture, silica glass was added to obtain a dental material composition (2). When a cured product of the dental material composition (2) was subjected to a bending test, the cured product had elastic modulus of 8.0 GPa, breaking strength of 192 MPa, and breaking energy of 46 mJ.

Example 3

The same reaction as that of Example 1 was performed except that the amounts of NBDI, ED-600, and HEA to be added were changed to amounts described in Table 1, to obtain 50 g of a composition containing a urethane urea acrylate (D-3) (urethane urea type (meth)acrylate (D-3)). The composition had a viscosity of 1720 mPa·s at 65° C. The composition had a refractive index of 1.5045 at 25° C. The IR spectrum of the composition containing a urethane urea acrylate (D-3) is shown in FIG. 1.

24.0 parts by weight of the obtained composition containing a urethane urea acrylate (D-3) and 6.0 parts by weight of EBADMA (2.6) were added into a container. The mixture was stirred to uniformity at 50° C. to obtain a monomer composition (dental material monomer composition) (3).

CQ and DMAB2-BE were added in the same manner as in Example 1 except that a monomer composition (1) was changed to the monomer composition (3). Furthermore, to the mixture, silica glass was added to obtain a dental material composition (3). When a cured product of the dental material composition (3) was subjected to a bending test, the cured product had elastic modulus of 7.3 GPa, breaking strength of 180 MPa, and breaking energy of 39 mJ.

Example 4

The same reaction as that of Example 1 was performed except that 22.94 parts by weight of NBDI was changed to 20.52 parts by weight of XDI; 25.06 parts by weight of HEA was changed to 27.52 parts by weight of HPA; and the amount of ED-600 to be added was changed to an amount described in Table 1, to obtain 50 g of a composition containing a urethane urea acrylate (D-4) (urethane urea type (meth)acrylate (D-4)). The composition had a viscosity of 640 mPa·s at 65° C. The composition had a refractive index of 1.5153 at 25° C.

24.0 parts by weight of the obtained composition containing a urethane urea acrylate (D-4) and 6.0 parts by weight of EBADMA (2.6) were added into a container. The mixture was stirred to uniformity at 50° C. to obtain a monomer composition (dental material monomer composition) (4).

CQ and DMAB2-BE were added in the same manner as in Example 1 except that a monomer composition (1) was changed to the monomer composition (4). Furthermore, to the mixture, silica glass was added to obtain a dental material composition (4). When a cured product of the dental material composition (4) was subjected to a bending test, the cured product had elastic modulus of 8.2 GPa, breaking strength of 199 MPa, and breaking energy of 40 mJ.

Example 5

The same reaction as that of Example 4 was performed except that the amounts of XDI, ED-600, and HPA to be added were changed to amounts described in Table 1, to obtain 50 g of a composition containing a urethane urea acrylate (D-5) (urethane urea type (meth)acrylate (D-5)). The composition had a viscosity of 960 mPa·s at 65° C. The composition had a refractive index of 1.5152 at 25° C.

24.0 parts by weight of the obtained composition containing a urethane urea acrylate (D-5) and 6.0 parts by weight of EBADMA (2.6) were added into a container. The mixture was stirred to uniformity at 50° C. to obtain a monomer composition (dental material monomer composition) (5).

CQ and DMAB2-BE were added in the same manner as in Example 1 except that a monomer composition (1) was changed to the monomer composition (5). Furthermore, to the mixture, silica glass was added to obtain a dental material composition (5). When a cured product of the dental material composition (5) was subjected to a bending test, the cured product had elastic modulus of 8.3 GPa, breaking strength of 210 MPa, and breaking energy of 40 mJ.

Example 6

The same reaction as that of Example 4 was performed except that the amounts of XDI, ED-600, and HPA to be added were changed to amounts described in Table 1, to obtain 50 g of a composition containing a urethane urea acrylate (D-6) (urethane urea type (meth)acrylate (D-6)). The composition had a viscosity of 1560 mPa·s at 65° C. The composition had a refractive index of 1.5149 at 25° C. The IR spectrum of the composition containing a urethane urea acrylate (D-6) is shown in FIG. 2.

12.0 parts by weight of the obtained composition containing a urethane urea acrylate (D-6) and 3.0 parts by weight of EBADMA (2.6) were added into a container. The mixture was stirred to uniformity at 50° C. to obtain a monomer composition (dental material monomer composition) (6).

CQ and DMAB2-BE were added in the same manner as in Example 1 except that a monomer composition (1) was changed to the monomer composition (6). Furthermore, to the mixture, silica glass was added to obtain a dental material composition (6). When a cured product of the dental material composition (6) was subjected to a bending test, the cured product had elastic modulus of 8.0 GPa, breaking strength of 191 MPa, and breaking energy of 38 mJ.

Example 7

The same reaction as that of Example 1 was performed except that 22.94 parts by weight of NBDI was changed to 25.05 parts by weight of TMXDI, and the amounts of HEA and ED-600 to be added were changed to amounts described in Table 1, to obtain 50 g of a composition containing a urethane urea acrylate (D-7) (urethane urea type (meth)acrylate (D-7)). The composition had a viscosity of 2210 mPa·s at 65° C. The composition had a refractive index of 1.5171 at 25° C.

12.0 parts by weight of the obtained composition containing a urethane urea acrylate (D-7) and 3.0 parts by weight of EBADMA (2.6) were added into a container. The mixture was stirred to uniformity at 50° C. to obtain a monomer composition (dental material monomer composition) (7).

CQ and DMAB2-BE were added in the same manner as in Example 1 except that a monomer composition (1) was changed to the monomer composition (7). Furthermore, to the mixture, silica glass was added to obtain a dental material composition (7). When a cured product of the dental material composition (7) was subjected to a bending test, the cured product had elastic modulus of 8.5 GPa, breaking strength of 175 MPa, and breaking energy of 30 mJ.

Example 8

The same reaction as that of Example 7 was performed except that the amounts of TMXDI, ED-600, and HPA to be added were changed to amounts described in Table 1, to obtain 50 g of a composition containing a urethane urea acrylate (D-8) (urethane urea type (meth)acrylate (D-8)). The composition had a viscosity of 2470 mPa·s at 65° C. The composition had a refractive index of 1.5166 at 25° C.

12.0 parts by weight of the obtained composition containing a urethane urea acrylate (D-8) and 3.0 parts by weight of EBADMA (2.6) were added into a container. The mixture was stirred to uniformity at 50° C. to obtain a monomer composition (dental material monomer composition) (8).

CQ and DMAB2-BE were added in the same manner as in Example 1 except that a monomer composition (1) was changed to the monomer composition (8). Furthermore, to the mixture, silica glass was added to obtain a dental material composition (8). When a cured product of the dental material composition (8) was subjected to a bending test, the cured product had elastic modulus of 8.2 GPa, breaking strength of 178 MPa, and breaking energy of 34 mJ.

Example 9

The same reaction as that of Example 7 was performed except that the amounts of TMXDI, ED-600, and HPA to be added were changed to amounts described in Table 1, to obtain 50 g of a composition containing a urethane urea acrylate (D-9) (urethane urea type (meth)acrylate (D-9)). The composition had a viscosity of 3400 mPa·s at 65° C. The composition had a refractive index of 1.5164 at 25° C. The IR spectrum of the composition containing urethane urea acrylate (D-9) is shown in FIG. 3.

12.0 parts by weight of the obtained composition containing a urethane urea acrylate (D-9) and 3.0 parts by weight of EBADMA (2.6) were added into a container. The mixture was stirred to uniformity at 50° C. to obtain a monomer composition (dental material monomer composition) (9).

CQ and DMAB2-BE were added in the same manner as in Example 1 except that a monomer composition (1) was changed to the monomer composition (9). Furthermore, to the mixture, silica glass was added to obtain a dental material composition (9). When a cured product of the dental material composition (9) was subjected to a bending test, the cured product had elastic modulus of 7.8 GPa, breaking strength of 178 MPa, and breaking energy of 39 mJ.

Example 10

The same reaction as that of Example 1 was performed except that 25.06 parts by weight of HEA was changed to 26.48 parts by weight of HEMA, and the amounts of NBDI and ED-600 to be added were changed to amounts described in Table 1, to obtain 50 g of a composition containing a urethane urea methacrylate (D-10) (urethane urea type (meth)acrylate (D-10)). The composition had a viscosity of 1030 mPa·s at 65° C. The composition had a refractive index of 1.5018 at 25° C.

12.0 parts by weight of the obtained composition containing a urethane urea acrylate (D-10) and 3.0 parts by weight of EBADMA (2.6) were added into a container. The mixture was stirred to uniformity at 50° C. to obtain a monomer composition (dental material monomer composition) (10).

CQ and DMAB2-BE were added in the same manner as in Example 1 except that a monomer composition (1) was changed to the monomer composition (10). Furthermore, to the mixture, silica glass was added to obtain a dental material composition (10). When a cured product of the dental material composition (10) was subjected to a bending test, the cured product had elastic modulus of 8.3 GPa, breaking strength of 194 MPa, and breaking energy of 30 mJ.

Example 11

The same reaction as that of Example 10 was performed except that the amounts of NBDI, ED-600, and HEMA to be added were changed to amounts described in Table 1, to obtain 50 g of a composition containing a urethane urea methacrylate (D-11) (urethane urea type (meth)acrylate (D-11)). The composition had a viscosity of 1340 mPa·s at 65° C. The composition had a refractive index of 1.5019 at 25° C.

12.0 parts by weight of the obtained composition containing a urethane urea acrylate (D-11) and 3.0 parts by weight of EBADMA (2.6) were added into a container. The mixture was stirred to uniformity at 50° C. to obtain a monomer composition (dental material monomer composition) (11).

CQ and DMAB2-BE were added in the same manner as in Example 1 except that a monomer composition (1) was changed to the monomer composition (11). Furthermore, to the mixture, silica glass was added to obtain a dental material composition (11). When a cured product of the dental material composition (11) was subjected to a bending test, the cured product had elastic modulus of 8.4 GPa, breaking strength of 218 MPa, and breaking energy of 42 mJ.

Example 12

The same reaction as that of Example 10 was performed except that the amounts of NBDI, ED-600, and HEMA to be added were changed to amounts described in Table 1, to obtain 50 g of a composition containing a urethane urea methacrylate (D-12) (urethane urea type (meth)acrylate (D-12)). The composition had a viscosity of 2440 mPa·s at 65° C. The composition had a refractive index of 1.5017 at 25° C. The IR spectrum of the composition containing a urethane urea acrylate (D-12) is shown in FIG. 4.

12.0 parts by weight of the obtained composition containing a urethane urea acrylate (D-12) and 3.0 parts by weight of EBADMA (2.6) were added into a container. The mixture was stirred to uniformity at 50° C. to obtain a monomer composition (dental material monomer composition) (12).

CQ and DMAB2-BE were added in the same manner as in Example 1 except that a monomer composition (1) was changed to the monomer composition (12). Furthermore, to the mixture, silica glass was added to obtain a dental material composition (12). When a cured product of the dental material composition (12) was subjected to a bending test, the cured product had elastic modulus of 7.9 GPa, breaking strength of 183 MPa, and breaking energy of 31 mJ.

Example 13

The same reaction as that of Example 10 was performed except that 21.63 parts by weight of NBDI was changed to 21.86 parts by weight of TMHDI, and the amounts of ED-600 and HEMA to be added were changed to amounts described in Table 1, to obtain 50 g of a composition containing a urethane urea methacrylate (D-13) (urethane urea type (meth)acrylate (D-13)). The composition had a viscosity of 310 mPa·s at 65° C. The composition had a refractive index of 1.4846 at 25° C.

12.0 parts by weight of the obtained composition containing a urethane urea acrylate (D-13) and 3.0 parts by weight of EBADMA (2.6) were added into a container. The mixture was stirred to uniformity at 50° C. to obtain a monomer composition (dental material monomer composition) (13).

CQ and DMAB2-BE were added in the same manner as in Example 1 except that a monomer composition (1) was changed to the monomer composition (13). Furthermore, to the mixture, silica glass was added to obtain a dental material composition (13). When a cured product of the dental material composition (13) was subjected to a bending test, the cured product had elastic modulus of 7.4 GPa, breaking strength of 180 MPa, and breaking energy of 32 mJ.

Example 14

The same reaction as that of Example 13 was performed except that the amounts of TMHDI, ED-600, and HEMA to be added were changed to amounts described in Table 1, to obtain 50 g of a composition containing a urethane urea methacrylate (D-14) (urethane urea type (meth)acrylate (D-14)). The composition had a viscosity of 320 mPa·s at 65° C. The composition had a refractive index of 1.4851 at 25° C.

12.0 parts by weight of the obtained composition containing a urethane urea acrylate (D-14) and 3.0 parts by weight of EBADMA (2.6) were added into a container. The mixture was stirred to uniformity at 50° C. to obtain a monomer composition (dental material monomer composition) (14).

CQ and DMAB2-BE were added in the same manner as in Example 1 except that a monomer composition (1) was changed to the monomer composition (14). Furthermore, to the mixture, silica glass was added to obtain a dental material composition (14). When a cured product of the dental material composition (14) was subjected to a bending test, the cured product had elastic modulus of 6.8 GPa, breaking strength of 189 MPa, and breaking energy of 48 mJ.

Example 15

The same reaction as that of Example 13 was performed except that the amounts of TMHDI, ED-600, and HEMA to be added were changed to amounts described in Table 1, to obtain 50 g of a composition containing a urethane urea methacrylate (D-15) (urethane urea type (meth)acrylate (D-15)). The composition had a viscosity of 560 mPa·s at 65° C. The composition had a refractive index of 1.4841 at 25° C. The IR spectrum of the composition containing a urethane urea acrylate (D-15) is shown in FIG. 5.

12.0 parts by weight of the obtained composition containing a urethane urea acrylate (D-15) and 3.0 parts by weight of EBADMA (2.6) were added into a container. The mixture was stirred to uniformity at 50° C. to obtain a monomer composition (dental material monomer composition) (15).

CQ and DMAB2-BE were added in the same manner as in Example 1 except that a monomer composition (1) was changed to the monomer composition (15). Furthermore, to the mixture, silica glass was added to obtain a dental material composition (15). When a cured product of the dental material composition (15) was subjected to a bending test, the cured product had elastic modulus of 6.8 GPa, breaking strength of 179 MPa, and breaking energy of 33 mJ.

Comparative Example 1

0.012 parts by weight of CQ and 0.012 parts by weight of DMAB2-BE were added into 2.4 parts by weight of UDMA. The mixture was stirred to uniformity at room temperature. Furthermore, to the solution, 3.6 parts by weight of silica glass was added to obtain a dental material composition (16). When a cured product of the dental material composition (16) was subjected to a bending test, the cured product had elastic modulus of 5.9 GPa, breaking strength of 170 MPa, and breaking energy of 28 mJ.

TABLE 1

| | | Loading ratio | | | Properties of monomer | | Properties of cured body | | |
| | | Amine (A) (pbW) | Iso(thio) cyanate (B) (pbW) | Hydroxy (meth) acrylate (C) (pbW) | $NH_2/NCO$ *1 [mole ratio] | Viscosity [mPa·s] | Refractive index | Elastic modulus [GPa] | Breaking strength [MPa] | Breaking energy [mJ] |
|---|---|---|---|---|---|---|---|---|---|---|
| Examples | 1 | ED-600 2.00 | NBDI 22.94 | HEA 25.06 | 0.03 | 1330 | 1.5051 | 8.0 | 203 | 49 |
| | 2 | ED-600 3.28 | NBDI 22.57 | HEA 24.15 | 0.05 | 1440 | 1.5047 | 8.0 | 192 | 46 |
| | 3 | ED-600 6.31 | NBDI 21.70 | HEA 21.99 | 0.1 | 1720 | 1.5045 | 7.3 | 180 | 39 |
| | 4 | ED-600 1.96 | XDI 20.52 | HPA 27.52 | 0.03 | 640 | 1.5153 | 8.2 | 199 | 40 |
| | 5 | ED-600 3.22 | XDI 20.21 | HPA 26.57 | 0.05 | 960 | 1.5152 | 8.3 | 210 | 40 |
| | 6 | ED-600 6.22 | XDI 19.50 | HPA 24.28 | 0.1 | 1560 | 1.5149 | 8.0 | 191 | 38 |
| | 7 | ED-600 1.85 | TMXDI 25.05 | HEA 23.10 | 0.03 | 2210 | 1.5171 | 8.5 | 175 | 30 |
| | 8 | ED-600 3.03 | TMXDI 24.68 | HEA 22.29 | 0.05 | 2470 | 1.5166 | 8.2 | 178 | 34 |
| | 9 | ED-600 5.85 | TMXDI 23.80 | HEA 20.35 | 0.1 | 3400 | 1.5164 | 7.8 | 178 | 39 |

TABLE 1-continued

| | | Loading ratio | | | Properties of monomer | | Properties of cured body | | |
| | | Amine (A) (pbW) | Iso(thio)cyanate (B) (pbW) | Hydroxy (meth)acrylate (C) (pbW) | NH$_2$/NCO *1 [mole ratio] | Viscosity [mPa·s] | Refractive index | Elastic modulus [GPa] | Breaking strength [MPa] | Breaking energy [mJ] |
|---|---|---|---|---|---|---|---|---|---|---|
| | 10 | ED-600 1.89 | NBDI 21.63 | HEMA 26.48 | 0.03 | 1030 | 1.5018 | 8.3 | 194 | 30 |
| | 11 | ED-600 3.11 | NBDI 21.32 | HEMA 25.57 | 0.05 | 1340 | 1.5019 | 8.4 | 218 | 42 |
| | 12 | ED-600 6.01 | NBDI 20.64 | HEMA 23.45 | 0.1 | 2440 | 1.5017 | 7.9 | 183 | 31 |
| | 13 | ED-600 1.88 | TMHDI 21.86 | HEMA 26.20 | 0.03 | 310 | 1.4846 | 7.4 | 180 | 32 |
| | 14 | ED-600 3.08 | TMHDI 21.56 | HEMA 25.36 | 0.05 | 320 | 1.4851 | 6.8 | 189 | 48 |
| | 15 | ED-600 5.95 | TMHDI 20.84 | HEMA 23.21 | 0.1 | 560 | 1.4841 | 6.8 | 179 | 33 |
| Comparative Example | 1 | — | — | — | — | 170 | 1.4836 | 5.9 | 170 | 28 |

*1 Ratio (a/b) of number of moles of amino group of amine compound (A), a, to number of moles of iso(thio)cyanato group of iso(thio)cyanate compound (B), b It is found that the breaking strength of the cured product of the dental material composition containing the monomer composition (dental material monomer composition) of the present invention is largely increased as compared with the cured product of the conventional dental material composition. That is, the use of the monomer composition (dental material monomer composition) of the present invention having both toughness and rigidity was shown to provide an increase in the breaking strength of the cured product of the dental material composition.

The invention claimed is:

1. A (meth)acrylate (D) which is a reaction product of:
a bifunctional amino compound (A);
an iso(thio)cyanate compound (B) having two or more iso(thio)cyanato groups; and
a hydroxy (meth)acrylate compound (C) having one or more polymerizable groups,
wherein the amino compound (A) is a compound (a1) represented by the general formula (a1-1):

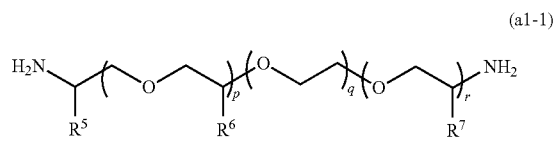

(a1-1)

wherein
R$^5$ to R$^7$ each represent a hydrogen atom or a methyl group;
p represents an integer of 0 to 100;
q represents an integer of 0 to 100;
r represents an integer of 1 to 100;
p+r satisfies an integer of 1 to 101; and
when a plurality of R$^6$ or R$^7$ are present, the plurality of R$^6$ or the plurality of R$^7$ may be the same as or different from each other,
an average molecular weight of the amino compound (A) is 100 to 600.

2. The (meth)acrylate (D) according to claim 1, wherein the (meth)acrylate (D) has a structure represented by the following general formula (D1) and a structure represented by the following general formula (D2):

(D1)

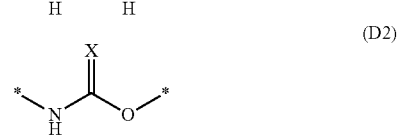

(D2)

wherein
X represents an oxygen atom or a sulfur atom; and
* represents a point of attachment.

3. The (meth)acrylate (D) according to claim 1, wherein the (meth)acrylate (D) is represented by the following general formula (1):

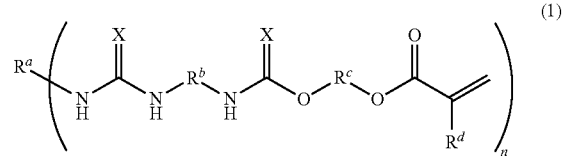

(1)

wherein
R$^a$ is a residue excluding all amino groups from a bifunctional amino compound (A1);
R$^b$ is a residue excluding all iso(thio)cyanato groups from an iso(thio)cyanate compound (B1) having two iso(thio)cyanato groups;
R$^c$ is a residue excluding one (meth)acryloyloxy group and one hydroxy group from the hydroxy (meth)acrylate compound (C);
R$^d$ represents a hydrogen atom or a methyl group;
X represents an oxygen atom or a sulfur atom;
n represents the number of all the amino groups contained in the amino compound (A); and a plurality of $R^b$, $R^c$, $R^d$, and X may each be the same as or different from each other.

4. The (meth)acrylate (D) according to claim 1, wherein the (meth)acrylate (D) is represented by the following general formula (2):

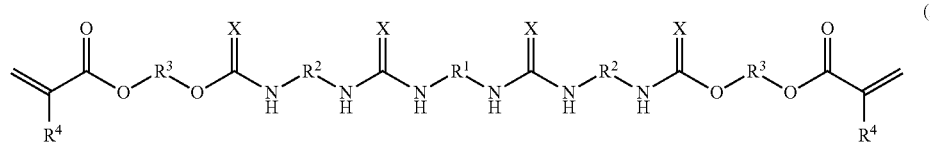

wherein
$R^1$ is a group in which a central part is bonded to two end parts;
the end part is bonded to a NH group adjacent to the end part;
the central part is a divalent hydrocarbon group;
an ethylene group contained in the divalent hydrocarbon group may be substituted with an oxyethylene group, or a propylene group contained in the divalent hydrocarbon group may be substituted with an oxypropylene group;
the end part is a methylene group which may have a substituent group;
each $R^2$ is independently a group in which a central part is bonded to two end parts;
the end part is bonded to a NH group adjacent to the end part;
the central part is a $C_{5-12}$ divalent aromatic hydrocarbon group, a $C_{5-12}$ divalent acyclic hydrocarbon group, or a $C_{5-12}$ divalent alicyclic hydrocarbon group;
the end part is a methylene group which may have a substituent group;
each $R^3$ is independently a $C_{2-6}$ linear alkylene group or a $C_{2-6}$ linear oxyalkylene group in which a hydrogen atom may be substituted with a $C_{1-3}$ alkyl group or a (meth)acryloyloxymethylene group;
$R^4$ each independently represents a hydrogen atom or a methyl group;
X is O or S; and
a plurality of $R^2$, $R^3$, $R^4$, and X may be the same as or different from each other.

5. The (meth)acrylate (D) according to claim 4, wherein in the general formula (2), $R^1$ is a group represented by the following formula (3):

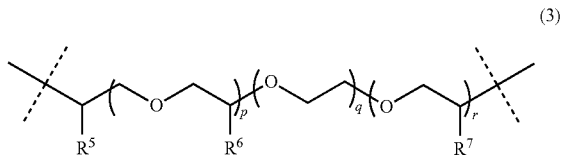

wherein
$R^5$ to $R^7$ each represent a hydrogen atom or a methyl group;
p represents an integer of 0 to 100;
q represents an integer of 0 to 100;
r represents an integer of 1 to 100;
p+r satisfies an integer of 1 to 101; and
when a plurality of $R^6$ or $R^7$ are present, the plurality of $R^6$ or the plurality of $R^7$ may be the same as or different from each other.

6. The (meth)acrylate (D) according to claim 4, wherein $R^1$ has an average molecular weight of 300 to 2000.

7. The (meth)acrylate (D) according to claim 4, wherein each $R^2$ is independently a group represented by the following formula (4), (5), (6), or (7):

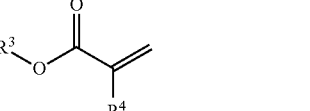

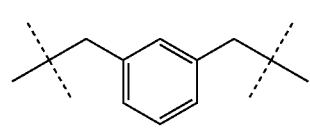

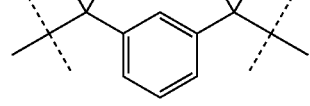

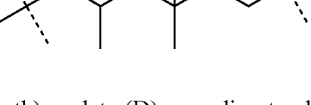

8. The (meth)acrylate (D) according to claim 4, wherein each $R^3$ is independently a $C_{2-6}$ linear alkylene group or a $C_{2-6}$ linear oxyalkylene group in which a hydrogen atom may be substituted with a $C_{1-3}$ alkyl group.

9. The (meth)acrylate (D) according to claim 1, wherein a ratio (a/b) of a number of moles of the amino groups of the amino compound (A), a, to a number of moles of the iso(thio)cyanato groups of the iso(thio)cyanate compound (B), b, is 0.01 to 0.20.

10. The (meth)acrylate (D) according to claim 1, wherein the iso(thio)cyanate compound (B) is at least one selected from the group consisting of hexamethylene diisocyanate, 2,2,4-trimethylhexane diisocyanate, 2,4,4-trimethylhexamethylene diisocyanate, pentamethylene diisocyanate, m-xylylene diisocyanate, isophorone diisocyanate, bis(isocyanatomethyl)cyclohexane, bis(isocyanatocyclohexyl)methane, 2,5-bis(isocyanatomethyl)bicyclo-[2.2.1]-heptane, 2,6-bis(isocyanatomethyl)bicyclo-[2.2.1]-heptane, tolylene diisocyanate, phenylene diisocyanate, and 4,4'-diphenylmethane diisocyanate.

11. The (meth)acrylate (D) according to claim 1, wherein the (meth)acrylate (D) has a viscosity of 1 to 100,000 mPa·s at 25° C.

12. A monomer composition comprising the (meth)acrylate (D) according to claim 1.

13. The monomer composition according to claim 12, wherein the monomer composition is a dental material monomer composition.

14. The monomer composition according to claim 12, wherein the monomer composition contains a polymerizable compound (E) containing at least one polymerizable group selected from a methacryloyl group and an acryloyl group excluding the (meth)acrylate (D).

15. A molded body obtained by curing the monomer composition according to claim 12.

16. A dental material composition comprising:
the monomer composition according to claim 12;
a polymerization initiator; and
a filler.

17. A dental material obtained by curing the dental material composition according to claim 16.

18. A method for producing a monomer composition, comprising the steps of:
(i) reacting a bifunctional amino compound (A) with an isocyanate compound (B) having two or more iso(thio)cyanato groups to obtain an intermediate; and
(ii) reacting the intermediate with a hydroxy (meth)acrylate compound (C) having one or more polymerizable groups,
wherein the amino compound (A) is a compound (a1) represented by the general formula (a1-1):

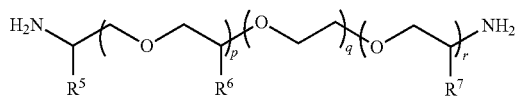

(a1-1)

wherein
$R^5$ to $R^7$ each represent a hydrogen atom or a methyl group;
p represents an integer of 0 to 100;
q represents an integer of 0 to 100;
r represents an integer of 1 to 100;
p+r satisfies an integer of 1 to 101; and
when a plurality of $R^6$ or $R^7$ are present, the plurality of $R^6$ or the plurality of $R^7$ may be the same as or different from each other,
an average molecular weight of the amino compound (A) is 100 to 600.

19. A method for producing a dental material, comprising the steps of:
injecting the dental material composition according to claim 16 into a casting mold; and
curing the dental material composition in the casting mold.

20. A dental material composition comprising:
a monomer composition comprising a (meth)acrylate (D);
a polymerization initiator; and
a filler;
wherein the (meth)acrylate (D) is a reaction product of:
a bifunctional amino compound (A);
an iso(thio)cyanate compound (B) having two or more iso(thio)cyanato groups; and
a hydroxy (meth)acrylate compound (C) having one or more polymerizable groups;
wherein the amino compound (A) is a compound (a1) represented by the general formula (a1-1),

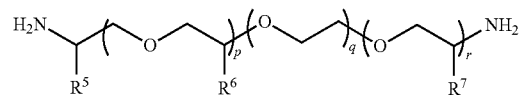

(a1-1)

wherein
$R^5$ to $R^7$ each represent a hydrogen atom or a methyl group;
p represents an integer of 0 to 100;
q represents an integer of 0 to 100;
r represents an integer of 1 to 100;
p+r satisfies an integer of 1 to 101; and
when a plurality of $R^6$ or $R^7$ are present, the plurality of $R^6$ or the plurality of $R^7$ may be the same as or different from each other.

21. A dental treatment method, comprising a step of:
curing a dental material composition comprising a monomer composition comprising a (meth)acrylate (D); and a polymerization initiator in a mouth,
wherein the (meth)acrylate (D) is a reaction product of:
an amine compound (A) having two or more amino groups;
an iso(thio)cyanate compound (B) having two or more iso(thio)cyanato groups; and
a hydroxy (meth)acrylate compound (C) having one or more polymerizable groups.

22. A dental treatment method, comprising a step of:
injecting a dental material composition comprising a monomer composition comprising the (meth)acrylate (D); and a polymerization initiator into a casting mold;
curing the dental material composition in the casting mold to obtain a cured product; and
applying the cured product to a tooth defect site,
wherein the (meth)acrylate (D) is a reaction product of:
an amine compound (A) having two or more amino groups;
an iso(thio)cyanate compound (B) having two or more iso(thio)cyanato groups; and
a hydroxy (meth)acrylate compound (C) having one or more polymerizable groups.

* * * * *